(12) United States Patent
Beilinson et al.

(10) Patent No.: US 10,344,295 B2
(45) Date of Patent: Jul. 9, 2019

(54) METHODS AND COMPOSITIONS FOR PROVIDING RESISTANCE TO GLUFOSINATE

(71) Applicant: AgBiome, Inc., Research Triangle Park, NC (US)

(72) Inventors: Vadim Beilinson, Cary, NC (US); James R. Henriksen, Cary, NC (US); Janice C. Jones, Apex, NC (US); Rebekah Deter Kelly, Durham, NC (US); Amy Shekita, Cary, NC (US)

(73) Assignee: AGBIOME, INC., Research Triangle Park, NC (US)

( * ) Notice: Subject to any disclaimer, the term of this patent is extended or adjusted under 35 U.S.C. 154(b) by 0 days.

(21) Appl. No.: 15/531,010

(22) PCT Filed: Dec. 18, 2015

(86) PCT No.: PCT/US2015/066648
§ 371 (c)(1),
(2) Date: May 26, 2017

(87) PCT Pub. No.: WO2016/100804
PCT Pub. Date: Jun. 23, 2016

(65) Prior Publication Data
US 2017/0362604 A1  Dec. 21, 2017

Related U.S. Application Data

(60) Provisional application No. 62/189,505, filed on Jul. 7, 2015, provisional application No. 62/094,697, filed on Dec. 19, 2014, provisional application No. 62/094,782, filed on Dec. 19, 2014.

(51) Int. Cl.
*C12N 15/82* (2006.01)
*C12N 9/10* (2006.01)
*A01N 57/20* (2006.01)

(52) U.S. Cl.
CPC ......... *C12N 15/8277* (2013.01); *A01N 57/20* (2013.01); *C12N 9/1029* (2013.01); *C12N 15/8209* (2013.01); *C12Y 203/01183* (2013.01)

(58) Field of Classification Search
None
See application file for complete search history.

(56) References Cited

U.S. PATENT DOCUMENTS

2009/0158469 A1  6/2009  Hasegawa et al.
2011/0195845 A1*  8/2011  Lira ..................... C12N 15/821
                                          504/201

FOREIGN PATENT DOCUMENTS

WO  2008/070845 A2  6/2008

OTHER PUBLICATIONS

GenBank EXL30079.1, Phosphinothricin N-acetyltransferase [*Pseudomonas syringae* pv. syringae str. B301 D-R], Mar. 6, 2014 (Year: 2014).*
GenBank KFD11103.1, Phosphinothricin N-acetyltransferase [*Serratia nnarcescens* subsp. nnarcescens ATCC 13880], Jul. 28, 2014 (Year: 2014).*
International Search Report and Written Opinion of PCT/US2015/066648, dated Mar. 29, 2016, 20 pages.
Database UniProt, "SubName: Full=N-acetyltransferase GCN5 {EC0:0000313:EMBL:EIK93778.1}", XP002754896, retrieved from EBI accession No. UNIPROT:I4MX38, Sep. 5, 2012, 1 page.
Proenca et al., "Draft Genome Sequence of *Pseudomonas* sp. Strain M47T1, Carried by Bursaphelenchus xylophilus Isolated from Pinus pinaster", Journal of Bacteriology, vol. 194, No. 17, Sep. 1, 2012, pp. 4789-4790.
Database UniProt, "SubName: Full=Putative acetyltransferase {EC0:0000313:EMBL:CAQ45545.1}", XP002754897, retrieved from EBI accession No. UNIPROT:B2FN24, Database accession No. B2FN24, Jun. 10, 2008, 1 page.
Crossman et al., "The complete genome, comparative and functional analysis of Stenotrophomonas maltophilia reveals an organism heavily shielded by drug resistance determinants", Genome Biology, Biomed Central Ltd., vol. 9, No. 4, Apr. 17, 2008, pp. R74.1-R74.13.
Database UniProt, "SubName: Full=GCN5-related N-acetyltransferase {EC0:0000313:EMBL:ABQ05801.1};", XP002754898, retrieved from EBI accession No. UNIPROT:A5FG65, Database accession No. A5FG65, Jun. 12, 2007, 1 page.
McBride et al., "Novel Features of the Polysaccharide-Digesting Gliding Bacterium Flavobacterium johnsoniae as Revealed by Genome Sequence Analysis", Applied and Environmental Microbiology, vol. 75. No. 21, Nov. 1, 2009, pp. 6864-6875.
Database UniProt, "SubName: Full=Phosphinothricin acetyl transferase {EC0:0000313:EMBL:AGE17134.1}", XP002754899, retrieved from EBI accession No. UNIPROT:L7ZIQ1, Database accession No. L7ZIQ1, Apr. 3, 2013, 1 page.
Kuo et al., "Phosphate limitation induces the intergeneric inhibition of Pseudomonas aeruginosa by Serratia marcescens isolated from paper machines", FEMS Microbiology Ecology, vol. 84, No. 3, Jun. 11, 2013, pp. 577-587.
Database UniProt, "SubName: Full=Acetyltransferase {EC0:0000313:EMBL:KFE51966.1}", XP002754900, retrieved from EBI accession No. UNIPROT:A0A085V953, Database accession No. A0A085V953, Oct. 29, 2014, 1 page.
Database UniProt, "R. equi phosphinothricin acetyltransferase (PAT), Seq ID:3", XP002754901, retrieved from EBI accession No. GSP:BAE45782, Database accession No. BAE45782, Dec. 6, 2012, 1 page.

(Continued)

Primary Examiner — Eileen B O Hara
(74) Attorney, Agent, or Firm — Kilpatrick Townsend & Stockton LLP

(57) ABSTRACT

Compositions and methods comprising polynucleotides and polypeptides that confer glufosinate resistance to a host cell are provided. Further provided are nucleic acid constructs, host cells, plants, plant cells, explants, seeds and grain having the sequence that confer glufosinate resistance. Various methods of employing these sequences are provided. Such methods include, for example, methods for producing a host cell, plant, plant cell, explant or seed having glufosinate resistance, and methods of controlling weeds in a field containing a crop employing the plants and/or seeds disclosed herein.

22 Claims, 5 Drawing Sheets

Specification includes a Sequence Listing.

(56) References Cited

OTHER PUBLICATIONS

Davies et al., "Crystal structure of a putative phosphinothricin acetyltransferase (PA4866) from Pseudomonas aeruginosa PAC1", Proteins: Structure, Function, and Bioinformatics, vol. 61, No. 3, Nov. 15, 2005, pp. 677-679.

Madduri et al., "Expression of phosphinothricin N-acetyltransferase in *Escherichia coli* and Pseudomonas fluorescens: Influence of mRNA secondary structure, host, and other physiological conditions", Protein Expression and Purification, Academic Press, San Diego, CA, vol. 55, No. 2, Sep. 8, 2007, pp. 352-360.

\* cited by examiner

Figure 2

CLUSTAL 2.1 multiple sequence alignment

```
SEQ ID NO: 5   ----MAVLIR------DAGPADIAAITAIYAVEVTDFVNTYEYDIPDASEMLRRMRDIID  50
SEQ ID NO: 9   ----MTTLSAPVLSLLDATPDDMAAVLRIYTQHVLYGAASFEEQPPTLAEMQLRLSKVRE  56
SEQ ID NO: 1   ----MSKTTVR-----IAQVSDAQAIQAIYAPMVESTTISFELEPPSVEEMAMRIESTLL  51
SEQ ID NO: 3   ------MLIR------DTVTEDLPSILDIHNDAIRNTTAIWDETEVGLDERMDWLDGRLR  48
SEQ ID NO: 11  MKTNMTYTIR------DALLTDMPAVLDIYNDAVLNTTAIWNEQPVDLGNREAWFAARQT  54
SEQ ID NO: 7   ----MSVILR------PATVNDLEKILEIVNHSILHTTANYSYDIQTIEVQTKWFEDKKA  50
                         :    *       :  .  :.           :

SEQ ID NO: 5   RGFPYLVAEIDG-QVAGYAYANTYRTRVAYQWTVENSVYVDAAFQGKGVGTGLLQALIDA  109
SEQ ID NO: 9   AGLPWLVAKSAG-VIVGYCYATPYRPRPAYRFTVEDSVYIAEGQQGKGIGRALLSALIAR  115
SEQ ID NO: 1   T-YPYLVAVRDG-QVIGYAYASQHRAREAYRWSVDVTVYISPEAHRSGVGRALYDVLLPT  109
SEQ ID NO: 3   AGYPVLTAVVDG-AVAGYASYAQWRPKSGYRLTVEHSVYVGSDFHRRGIASALMAELIAR  107
SEQ ID NO: 11  QAYPILVVVDDAGQVLGYSSFGDWRPFEGFRHTVEHSVYVRADQRGNGLGPLLMTALIER  114
SEQ ID NO: 7   KNLPIVVADLDG-EVVGFGSYGQFREKIGYQYTVEHSVYVVDNVIGKGIGSKLLTELIRL  109
                  * :..    .  : *;      *    .;: :*; :**;        *;. *  *;

SEQ ID NO: 5   CVARGYRQMVAVIGEP-TNTASIKLHERFGFELVGVFRGLGRKHGRWLDTVQMQRALGDG  168
SEQ ID NO: 9   CEQGPWRQMLAIVGDSAANRGSLALHQSLGFTSAGTLKAVGFKLGEWRDTQIMQRALGAG  175
SEQ ID NO: 1   LKKQGFHAAYAGIALP--NDGSVGLHEALGFAHIGTYPEVGFKHGAWRDVGYWRIALDST  167
SEQ ID NO: 3   ASAAGIHALVGVIESR--NTTSIALHEKFGFVTVGQMPEVGIKFDRWLDLTLMQLTL---  162
SEQ ID NO: 11  ARTCDKHMMVAAIESG--NAASIHLHQKQGFITTGQMPQVGTKFGRWLDLTFMQLDLSPG  172
SEQ ID NO: 7   AKEQGYHVMIGAIDAD--NAGSITFHEKFGFVATGTIREVGYKFDHWLDLVFMQLILK--  165
                :  ..;     * *: :*: **   *    :* *  * *    ;  *

SEQ ID NO: 5   ADTAPSNE-------  176
SEQ ID NO: 9   GNRHP----------  180
SEQ ID NO: 1   NPPKLPVLFSEISLF  182
SEQ ID NO: 3   ---------------
SEQ ID NO: 11  ASAPPSQAPASTPVA  187
SEQ ID NO: 7   ---------------
```

METHODS AND COMPOSITIONS FOR PROVIDING RESISTANCE TO GLUFOSINATE

CROSS REFERENCE TO RELATED APPLICATION

This Application claims the priority to U.S. Provisional Application No. 62/094,697, filed on Dec. 19, 2014, U.S. Provisional App. No. 62/094,782, filed Dec. 19, 2014 and U.S. Provisional Application No. 62/189,505, filed on Jul. 7, 2015, each of which are incorporated by reference in their entirety.

FIELD OF THE INVENTION

This invention is in the field of molecular biology. More specifically, this invention pertains to method and compositions comprising polypeptides which confer resistance to glufosinate and methods of their use.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named AgB010_SEQLIST.txt, created on Dec. 14, 2015 and having a size of 14.5 KB and is filed concurrently with the specification. The sequence listing contained in this ASCII formatted document is part of the specification and is herein incorporated by reference in its entirety.

BACKGROUND OF THE INVENTION

Tolerance to specific herbicides can be conferred by engineering genes into host cells and such genes find use as both selectable markers and, when employed in crops, as a method to control weeds. In some cases these enzymes, and the nucleic acids that encode them, originate in a plant. In other cases, they are derived from other organisms, such as microbes. See, e.g., Padgette et al. (1996) "New weed control opportunities: Development of soybeans with a Roundup Ready® gene" and Vasil (1996) "Phosphinothricin-resistant crops," both in *Herbicide-Resistant Crops*, ed. Duke (CRC Press, Boca Raton, Fla.) pp. 54-84 and pp. 85-91. Indeed, transgenic plants have been engineered to express a variety of herbicide tolerance genes from a variety of organisms.

While a number of herbicide-tolerant crop plants are presently commercially available, improvements in every aspect of crop production, weed control options, extension of residual weed control, and improvement in crop yield are continuously in demand. Particularly, due to local and regional variation in dominant weed species, as well as preferred crop species, a continuing need exists for customized systems of crop protection and weed management which can be adapted to the needs of a particular region, geography, and/or locality. A continuing need therefore exists for compositions and methods of crop protection and weed management.

BRIEF SUMMARY OF THE INVENTION

Compositions and methods comprising polynucleotides and polypeptides that confer glufosinate resistance to a host cell are provided. Further provided are nucleic acid constructs, host cells, plants, plant cells, explants, seeds and grain having the sequence that confers glufosinate resistance. Various methods of employing these sequences are provided. Such methods include, for example, methods for producing a host cell, plant, plant cell, explant or seed having glufosinate resistance, methods to employ the sequences as selectable markers, and methods of controlling weeds in a field containing a crop employing the plants and/or seeds disclosed herein.

BRIEF DESCRIPTION OF THE DRAWINGS

FIG. 2 provides an alignment of the amino acid sequences set forth in SEQ ID NO: 1, 3, 5, 7, 9, and 11.

DETAILED DESCRIPTION OF THE INVENTION

Figure 1:
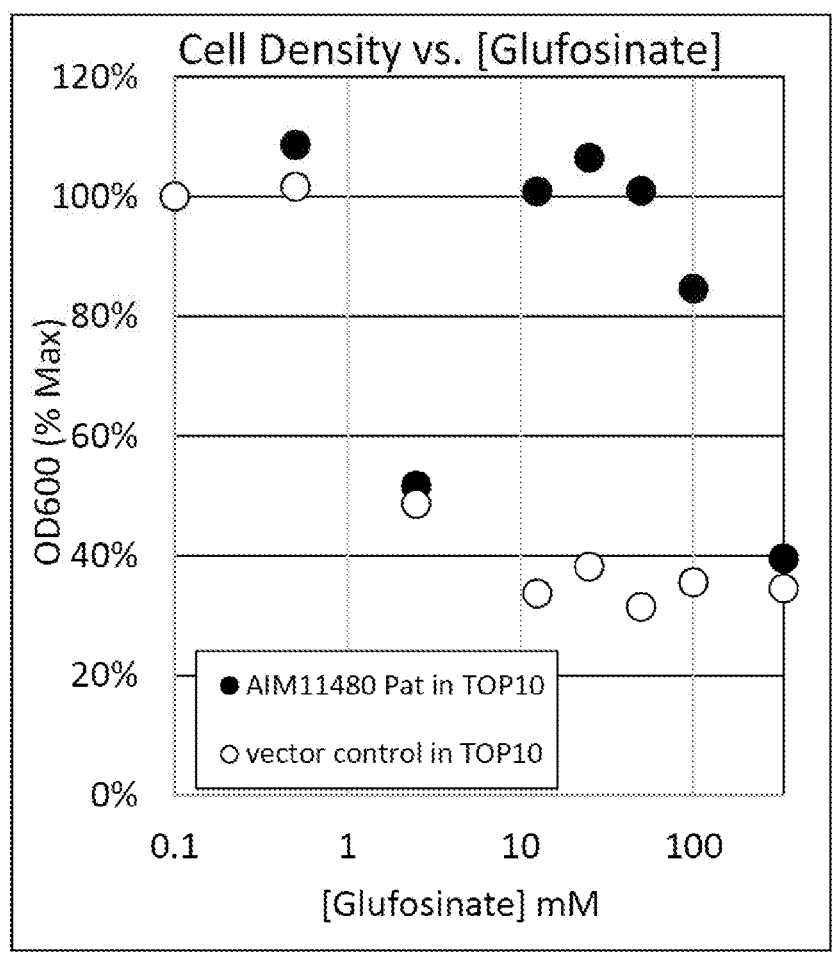
FIG. 1 provides a minimal inhibitory concentration experiment. A polynucleotide encoding SEQ ID NO: 1 was transformed into *E. coli* cells for protein expression with an N-terminal maltose binding protein. The resulting *E. coli* clone was analyzed for the ability to grow in the presence of glufosinate. The *E. coli* expressing SEQ ID NO:1 were able to grow in the liquid media with concentrations of glufosinate reaching 100 mM, while control *E. coli* was not able to tolerate more than 1 mM glufosinate in minimum-inhibitory concentration experiments.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Compositions

A. Polypeptides that Confers Glufosinate Resistance and Polynucleotides Encoding the Same As used herein, a polypeptide that "confers glufosinate resistance" refers to a polypeptide which, when expressed in a host cell, imparts resistance of the host cell to glufosinate.

Polypeptides are provided that confer glufosinate resistance is set forth in SEQ ID NO: 1, 3, 5, 7, 9, and 11 and further provided are various active variants or fragments thereof and the polynucleotides encoding the same. The polynucleotides encoding SEQ ID NO: 1, 3, 5, 7, 9, and 11 are set forth in SEQ ID NO: 2, 4, 6, 8, 10, and 12, respectively. Various methods to assay for an "increased resistance" to glufosinate are discussed elsewhere herein.

i. Active Fragments and Variants of Sequences that Confer Glufosinate Resistance Fragments and variants of polynucleotides (RNA and DNA) and polypeptides that confer glufosinate resistance can be employed in the methods and compositions disclosed herein. By "fragment" is intended a portion of the polynucleotide or a portion of the amino acid sequence and hence protein encoded thereby. Fragments of a polynucleotide may encode protein fragments that retain the ability to confer glufosinate resistance on a host cell. In specific embodiments, a fragment of a recombinant polynucleotide or a recombinant polynucleotide construct comprises at least one junction of the two or more chemically linked or operably linked nucleic acid segments which are not found directly joined in nature. Fragments of a nucleotide sequence comprise at least 16, 20, 50, 75, 100, 125, 150, 175, 200, 225, 250, 275, 300, 325, 350, 375, 400, 425, 450, 475, 500, 525, 549 contiguous nucleotides, or up to the number of nucleotides present in a full-length polynucleotide as set forth in SEQ ID NO: 2, 4, 6, 8, 10, or 12. Thus, a fragment of a polynucleotide that encodes a biologically active portion of a polypeptide that retains the ability to confer glufosinate resistance on a host cell will encode at least 25, 30, 40, 50, 60, 70, 75, 80, 90, 100, 110, 120, 125, 130, 140, 150, 160, 170, 175, 180, contiguous amino acids, or up to the total number of amino acids present in a full-length polypeptide as set forth in SEQ ID NO: 1, 3, 5, 7, 9, or 11. Fragments of a polypeptide may range from 25, 30, 40, 50, 60, 70, 75, 80, 90, 100, 110, 120, 125, 130, 140, 150, 160, 170, 175, 180 amino acids up to the full-length of the polypeptide. In specific embodiments, such polypeptide fragments are active fragment, and in still other embodiments, the polypeptide fragment comprises a recombinant polypeptide fragment. As used herein, a fragment of a recombinant polypeptide comprises at least one of a combination of two or more chemically linked amino acid segments which are not found directly joined in nature.

By "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptide that confers glufosinate resistance. Naturally occurring variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a polypeptide that confer glufosinate resistance. Generally, variants of a particular polynucleotide disclosed herein will have at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to SEQ ID NO: 2, 4, 6, 8, 10 or 12 determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 1, 3, 5, 7, 9, or 11 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to SEQ ID NO: 1, 3, 5, 7, 9, or 11.

"Variant" protein is intended to mean a protein derived from the native protein by deletion or addition of one or more amino acids at one or more internal sites in the native protein and/or substitution of one or more amino acids at one or more sites in the native protein. Variant proteins encompassed herein are biologically active, that is they continue to possess the desired biological activity of the native protein, that is, confer glufosinate resistance to a host cell as described herein. Such variants may result from, for example, genetic polymorphism or from human manipulation. Biologically active variants of a polypeptide that confers glufosinate resistance will have at least about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or more sequence identity to SEQ ID NO: 1, 3, 5, 7, 9, or 11 as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The polypeptides that confer glufosinate resistance and the active variants and fragments thereof may be altered in various ways including amino acid substitutions, deletions, truncations, and insertions and through rational design modeling as discussed elsewhere herein. Methods for such manipulations are generally known in the art. For example, amino acid sequence variants and fragments of the polypeptides that confer glufosinate resistance can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference in their entirety. Conservative substitutions, such as exchanging one amino acid with another having similar properties, may be optimal.

The mutations that will be made in the DNA encoding the variant should not place the sequence out of reading frame and optimally will not create complementary regions that could produce secondary mRNA structure. See, EP Patent Application Publication No. 75,444.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

A "recombinant polynucleotide construct" comprises two or more operably linked nucleic acid segments which are not found operably linked in nature. Non-limiting examples of recombinant polynucleotide constructs include a polynucleotide of interest or active variant or fragment thereof operably linked to heterologous sequences which aid in the expression, autologous replication, and/or genomic insertion of the sequence of interest. Such heterologous and operably linked sequences include, for example, promoters, termination sequences, enhancers, etc, or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

A "recombinant polypeptide" comprises a combination of two or more chemically linked amino acid segments which are not found directly joined in nature. In specific embodiments, the recombinant polypeptide comprises an additional chemically linked amino acid segment that is located either at the N-terminal, C-terminal or internal to the recombinant polypeptide. Alternatively, the chemically-linked amino acid segment of the recombinant polypeptide can be formed by deletion of at least one amino acid. The additional chemically linked amino acid segment or the deleted chemically linked amino acid segment can be of any length, including for example, 2, 3, 4, 5, 6, 7, 8, 9, 10, 15, 20 or amino acids.

II. Host Cells, Plants and Plant Parts

Host cells, plants, plant cells, plant parts, seeds, and grain having a heterologous copy of SEQ ID NO:1, 2, 3, 4, 5, 6, 7, 8, 9, 10, 11, 12 or an active variant or fragment thereof are provided. It is expected that those of skill in the art are knowledgeable in the numerous systems available for the introduction of a polypeptide or a nucleotide sequence disclosed herein into a host cell. No attempt to describe in detail the various methods known for providing sequences in prokaryotes or eukaryotes will be made.

By "host cell" is meant a cell which comprises a heterologous sequence of SEQ ID NO: 1, 2, 3, 4, 5, 6, 7, 8, 9, 10, 11, or 12. Host cells may be prokaryotic cells, such as *E. coli*, or eukaryotic cells such as yeast cells. Suitable host cells include the prokaryotes and the lower eukaryotes, such as fungi. Illustrative prokaryotes, both Gram-negative and Gram-positive, include *Enterobacteriaceae*, such as *Escherichia, Erwinia, Shigella, Salmonella,* and *Proteus; Bacillaceae; Rhizobiceae,* such as *Rhizohium; Spirillaceae,* such as photobacterium, *Zymomonas, Serratia, Aeromonas, Vibrio, Desulfovibrio, Spirillum; Lactobacillaceae, Pseudomonadaceae,* such as *Pseudomonas* and *Acetobacter; Azotobacteraceae* and *Nitrobacteraceae*. Among eukaryotes are fungi, such as *Phycomycetes* and *Ascomycetes*, which includes yeast, such as *Pichia pastoris, Saccharocmyces* and *Schizosaccharomyces,* and *Basidiomycetes* yeast, such as *Rhodotorula, Aureobasidium, Sporobolomyces,* and the like. Host cells can also be monocotyledonous or dicotyledonous plant cells.

In specific embodiments, the host cells, plants and/or plant parts have stably incorporated at least one heterologous polynucleotide encoding a polypeptide that confers glufosinate resistance to the host cell or an active variant or fragment thereof (i.e, SEQ ID NO: 1, 2, 3, 4, 5, 6, 7, 8, 9, 10, 11, or 12 or an active variant or fragment thereof).

The host cell, plants, plant cells and seed which express the heterologous polynucleotide encoding the polypeptide that confers glufosinate resistance can display an increased resistance to glufosinate. In one embodiment, an "increased resistance" to glufosinate in a host cell is assayed by growing the host cell expressing the polypeptide conferring glufosinate resistance in the presence of a concentration of glufosinate under conditions where the polypeptide is expressed at an effective level. Transgenic host cells that grows at a rate that is discernibly greater an the cell would grow if it did not contain SEQ ID NO: 1, 2, 3, 4, 5, 6, 7, 8, 9, 10, 11, 12 or an active variant or fragment thereof.

In other embodiments, an "increased resistance" to glufosinate in plants can further be demonstrated when plant host cells which display the increased resistance to the glufosinate are subjected to glufosinate and a dose/response curve is shifted to the right when compared with that provided by an appropriate control host cell. Such dose/response curves have "dose" plotted on the x-axis and "percentage injury", "herbicidal effect" etc. plotted on the y-axis. Plants which are substantially "resistant" or "tolerant" to the glufosinate exhibit few, if any, significant negative agronomic effects when subjected to the glufosinate at concentrations and rates which are typically employed by the agricultural community to kill weeds in the field.

In specific embodiments, the heterologous polynucleotide encoding the polypeptide that confers glufosinate resistance or an active variant or fragment thereof in the host cell, plant or plant part is operably linked to a constitutive, tissue-preferred, or other promoter for expression in the host cell or the plant of interest.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processes plant product or byproduct that retains the sequences disclosed herein, including for example, soymeal.

The polynucleotide encoding the polypeptide that confers glufosinate resistance and active variants and fragments thereof may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, *Arabidopsis*, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elhotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are of interest.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same germplasm, variety or line as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

III. Polynucleotide Constructs

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotides encoding a polypeptide that confer glufosinate resistance or active variant or fragment thereof can be provided in expression cassettes for expression in the plant of interest. The cassette can include 5' and 3' regulatory sequences operably linked to a polynucleotide encoding a polypeptide that confers glufosinate resistance or an active variant or fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. Additional gene(s) can be provided on multiple expression cassettes. Such an expression cassette is provided with a plurality of restriction sites and/or recombination sites for insertion of the polynucleotide encoding a polypeptide that confers glufosinate resistance or an active variant or fragment thereof to be under the transcriptional regulation of the regulatory regions.

The expression cassette can include in the 5'-3' direction of transcription, a transcriptional and translational initiation region (i.e., a promoter), a polynucleotide encoding a polypeptide that confers glufosinate resistance or an active variant or fragment thereof, and a transcriptional and translational termination region (i.e., termination region) functional in plants. The regulatory regions (i.e., promoters, transcriptional regulatory regions, and translational termination regions) and/or the polynucleotide encoding a polypeptide that confers glufosinate resistance or an active variant or fragment thereof may be native/analogous to the host cell or to each other. Alternatively, the regulatory regions and/or the polynucleotide encoding the polypeptide that confers glufosinate resistance or an active variant or fragment thereof may be heterologous to the host cell or to each other.

As used herein, "heterologous" in reference to a sequence is a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are modified from their original form and/or genomic locus, or the promoter is not the native promoter for the operably linked polynucleotide.

While it may be optimal to express the sequences using heterologous promoters, the native promoter sequences may be used. Such constructs can change expression levels of the polynucleotide encoding a polypeptide conferring glufosinate tolerance in the host cell, plant or plant cell. Thus, the phenotype of the host cell, plant or plant cell can be altered.

The termination region may be native with the transcriptional initiation region, may be native with the operably linked polynucleotide encoding a polypeptide that confers glufosinate resistance or active variant or fragment thereof, may be native with the host cell (i.e., plant cell), or may be derived from another source (i.e., foreign or heterologous) to the promoter, the polynucleotide encoding a polypeptide that confers glufosinate resistance or active fragment or variant thereof, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al, (1990) *Plant Cell* 2:1261-1272; Munroe et al, (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed host cell (i.e., a microbial cell or a plant cell). In specific embodiments, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference in their entirety.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEN leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385. See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used to express the various sequences disclosed herein, including the native promoter of the polynucleotide sequence of interest. The promoters can be selected based on the desired outcome. Such promoters include, for example, constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al (1990) *Plant Cell* 2:163-171); ubiquitin (Christensen et al. (1989) *Plant Mol. Biol.* 12:619-632 and Christensen et al (1992) *Plant Mol. Biol.* 18:675-689); pEMU (Last et al. (1991) *Theor. Appl. Genet.* 81:581-588); MAS (Velten et al. (1984) *EMBO*

J. 3:2723-2730); ALS promoter (U.S. Pat. No. 5,659,026); and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression of the polynucleotide encoding the polypeptide that confer tolerance to glufosinate within a particular plant tissue. Tissue-preferred promoters include those described in Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al (1997) *Transgenic Res.* 6(2):157-168, Rinehart et al. (1996) *Plant Physiol.* 112(3):1331-1341; Van Camp et al. (1996) *Plant Physiol.* 112(2):525-535; Canevascini et al. (1996) *Plant Physiol* 112(2):513-524; Yamamoto et al. (1994) *Plant Cell Physiol* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acari Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et a (1997) *Plant J.* 12(2):255-265; Kwon et al. (1994) *Plant Physiol.* 105:357-67; Yamamoto et al (1994) *Plant Cell Physiol.* 35(5):773-778; Gotor et al. (1993) *Plant* 3:509-18; Orozco et al (1993) *Plant Mol. Biol.* 23(6):1129-1138; and Matsuoka et al. (1993) *Proc. Natl Acad. Sci. USA* 90(20):9586-9590.

Meristem-preferred promoters can also be employed. Such promoter can drive expression in meristematic tissue, including, for example, the apical meristem, axillary buds, root meristems, cotyledon meristem and/or hypocotyl meristem. Non-limiting examples of meristem-preferred promoters include the shoot meristem specific promoter such as the *Arabidopsis* UFO gene promoter (Unusual Floral Organ) (U.S. Pat. No. 6,239,329), the meristem-specific promoters of FTM1, 2, 3 and SVP1, 2, 3 genes as discussed in US Patent App. 20120255064, and the shoot meristem-specific promoter disclosed in U.S. Pat. No. 5,880,330. Each of these references is herein incorporated by reference in their entirety.

The expression cassette can also comprise a selectable marker gene for the selection of transformed cells. In specific embodiments, the expression cassette comprises a polynucleotide encoding SEQ ID NO:1, 3, 5, 7, 9, 11 or an active variant or fragment thereof, and can therefore be used as a selectable marker in the presence of glufosinate. Additional selectable markers can also be employed for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et at (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad Sci. USA* 89:3952-3956; Baim et al. (1991) *Proc. Natl. Acad. Sci. USA* 88:5072-5076; Wyborski et al. (1991) *Nucleic Acid & Res.* 19:4647-4653; Hillenand-Wissman (1989) *Topics Mol. Struc. Biol.* 10:143-162.; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al, (1988) *Nature* 334:721-724. Such disclosures are herein incorporated by reference in their entirety. The above list of selectable marker genes is not meant to be limiting.

In certain embodiments, the polynucleotide construct may comprise a polynucleotide of interest. In specific, non-limiting embodiments, the polynucleotide of interest can be at least about 25, 50, 100, 200, 300, 400, 500, 700, 900 nucleotide or at least 1 kb, 2 kb, 3 kb, 4 kb, 5 kb, 6 kb, 7 kb, 8 kb, 9 kb, 10 kb, 11 kb, 12 kb, 1.3 kb, 14 kb, 15 kb, 20 kb, 40 kb, 60 kb or more. In other embodiments, the polynucleotide of interest is at least about 6 kb to about 15 kb, or about 6 kb to about 12 kb, or about 1 kb to about 12 kb.

Various changes in phenotype of the plant or plant cells are of interest upon introduction of the polynucleotide of interest. Such alterations include, but are not limited to, modifying the fatty acid composition in a plant, altering the amino acid content of a plant, altering a plant's pathogen defense mechanism, altering the plant's herbicide tolerance and the like. These results can be achieved by providing expression of heterologous products or increased expression of endogenous products in plants. Alternatively, the results can be achieved by providing for a reduction of expression of one or more endogenous products in the plant. These changes result in a change in phenotype of the transformed plant. To this end, the polynucleotide of interest can encode a protein or it can express a polynucleotide that acts to increase or decreases expression of a sequence of interest in the plant, and can include for example, miRNA or siRNA.

Genes of interest are reflective of the commercial markets and interests of those involved in the development of the crop. Crops and markets of interest change, and as developing nations open up world markets, new crops and technologies will emerge also. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like. See, for example, U.S. Pat. Nos. 5,703,049, 5,885, 801, 5,885,802, and 5,990,389, herein incorporated by reference. Other agronomically important genes encode latex, Floury 2, growth factors, seed storage factors, and transcription factors. Insect resistance genes may encode resistance to pests such as rootworm, cutworm, European Corn Borer, western corn root worm, fall army worm, corn ear worm, black cut worm, cotton ball worms, green stink bugs, soybean aphids, and/or nematodes, such as, soybean cyst nematodes or root not nematodes and the like. Such genes include, for example, *Bacillus thuringiensis* toxic protein genes (U.S. Pat. Nos. 5,366,892; 5,747,450; 5,736,514; 5,723.756; 5,593,881; and Geiser et al. (1986) *Gene* 48:109); and the like. Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like. Herbicide resistance traits may include genes coding for resistance to herbicides. Sterility genes can also be encoded in an expression cassette and provide an alternative to physical detasseling. U.S. Pat. No. 5,583,210. Other genes include kinases and those encoding compounds toxic to either male or female gametophytic development.

In other embodiments, the polynucleotide of interest may facilitate the transfer of non-agronomic traits. For example, the polynucleotide of interest can encodes non-proteins including antibodies for vaccines, micronutrients (e.g. folic acid, vitamin A), bio-pharmaceutical or veterinarian drugs.

IV. Method of Introducing

Various methods can be used to introduce a sequence of interest into a host cell, plant or plant part. "Introducing" is intended to mean presenting to the host cell, plant, plant cell or plant part the polynucleotide or polypeptide in such a manner that the sequence gains access to the interior of a cell. The methods disclosed herein do not depend on a particular method for introducing a sequence into a host cell, plant or plant part, only that the polynucleotide or polypeptides gains access to the interior of at least one cell. Methods for introducing polynucleotides or polypeptides into plants are known in the art including, but not limited to, stable transformation methods, transient transformation methods, and virus-mediated methods.

"Stable transformation" is intended to mean that the nucleotide construct introduced into a host cell or plant integrates into the genome of the host cell or plant and is capable of being inherited by the progeny thereof "Transient transformation" is intended to mean that a polynucleotide is introduced into the host cell or plant and does not integrate into the genome of the host cell or plant or a polypeptide is introduced into a host cell or plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. Nos. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Biotechnology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al, (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytehier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference in their entirety.

In other instances, the method of transformation employed for soybean is set forth in U.S. Pat. No. 7,473,822 and/or Paz et. al. (2010) "*Agrobacterium-mediated transformation of soybean and recovery of transgenic soybean plants*" Plant Transformation Facility at University of Iowa, 1-6, both of which are herein incorporated by reference in their entirety.

In specific embodiments, the sequences disclosed herein or active variant or fragments thereof can be provided to a plant using a variety of transient transformation methods. Such transient transformation methods include, but are not limited to, the introduction of a polypeptide that confers tolerance to glufosinate or active variants and fragments thereof directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al, (1994) *Proc. Natl. Acad. Sci.* 91: 2176-2180 and Hush et al. (1994) *The Journal of Cell Science* 107:775-784, all of which are herein incorporated by reference in their entirety.

In other embodiments, the polynucleotide encoding the polypeptide that confers glufosinate resistance or active variants or fragments thereof may be introduced into plants by contacting plants with a virus or viral nucleic acids. Generally, such methods involve incorporating a nucleotide construct of the invention within a DNA or RNA molecule. It is recognized that the sequence may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316, 931, and Porta et al. (1996) *Molecular Biotechnology* 5:209-221; herein incorporated by reference in their entirety.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference in their entirety. Other methods to target polynucleotides are set forth in WO 2009/114321 (herein incorporated by reference in its entirety), which describes "custom" meganucleases produced to modify plant genomes, in particular the genome of maize. See, also, Gao et al. (2010) *Plant Journal* 1:176-187.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference in their entirety. Other methods to target polynucleotides are set forth in WO 2009/114321 (herein incorporated by reference in its entirety), which describes "custom" meganucleases produced to modify plant genomes, in particular the genome of maize. See, also, Gao et al. (2010) *Plant Journal* 1:176-187. The CRISPR/Ca9 system can also be employed. See, Gaj et al. (2013) *Trends in Biotechnology* 7:397-405, herein incorporated by reference in its entirety.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Additional host cells of interest include, for example, prokaryotes including various strains of *E. coli* and other microbial strains. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al, (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235); Mosbach et al. (1983) *Nature* 302:543-545).

A variety of expression systems for yeast are known to those of skill in the art. Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers. See, for Example, Sherman et al. (1982) *Methoch in Yeast Genetics*, Cold Spring Harbor Laboratory.

V. Methods of Use

A. Methods for Increasing Expression and/or Concentration of at Least One Sequence that Confers Glufosinate Resistance or an Active Variant or Fragment Thereof in Host Cells Various methods are provided for the expression of a sequence that confer glufosinate resistance as set forth in SEQ ID NO: 1, 2, 3, 4, 5, 6, 7, 8, 9, 10, 11, 12 or active variants or fragments thereof in a host cell of interest. For example, the host cell of interest is transformed with the sequence that confers glufosinate resistance and the cells are cultured under conditions which allow for the expression of the sequence. As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique,* 3$^{rd}$ Ed., Wiley-Liss, New York and the references cited therein; Doyle and Griffiths (1997) *Mammalian Cell Culture: Essential Techniques* John Wiley and Sons, NY; Humason (1979) *Animal Tissue Techniques,* 4$^{th}$ Ed. W. H. Freeman and Company; and Ricciardelli, et al., (1989) *In vitro Cell Dev. Biol.* 25:1016-1024. For plant cell culture and regeneration see, Payne et al, (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin, Heidelberg, N.Y.); Jones, ed. (1984) *Plant Gene Transfer and Expression Protocols*, Humana Press, Totowa, N.J.; and *Plant Molecular Biology* (1993) R. R. D. Croy, ed. Bios Scientific Publishers, Oxford, U.K. ISBN 0 12 198370 6. Cell culture media in general are set forth in Atlas and Parks (eds.) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc. (St Louis, Mo.) ("Sigma-LSRCCC") and, e.g., *The Plant Culture Catalogue* and supplement (1997) also from Sigma-Aldrich, Inc. (St Louis, Mo.) ("Sigma-PCCS").

Further provided is a method for increasing the activity and/or concentration of a polypeptide that confers glufosinate resistance or an active variant or fragment thereof in a host cell, plant, plant cell, plant part, explant, or seed. Methods for assaying for an increase in glufosinate resistance are discussed in detail elsewhere herein.

In further embodiments, the concentration/level of the polypeptide that confers glufosinate resistance is increased in a host cell, a plant or plant part by at least 10%, 20%, 30%, 40%, 50%, 60%, 70%, 80%, 90%, 100%, 200%, 500%, 1000%, 5000%, or 10,000% relative to an appropriate control host cell, plant, plant part, or cell which did not express the sequence. In still other embodiments, the level of the polypeptide that confers resistance to glufosinate in the host cell, plant or plant part is increased by 10, 20, 30, 40, 50, 60, 70, 80, 90, 100 fold or more compared to the level in an appropriate control. Such an increase in the level of the polypeptide can be achieved in a variety of ways including, for example, by the expression of multiple copies of one or more polypeptide and/or by employing a promoter to drive higher levels of expression of the sequence.

In specific embodiments, the polynucleotide encoding the polypeptide that confers glufosinate resistance or active variants or fragments thereof is introduced into the host cell, plant, plant cell, explant or plant part. Subsequently, a host cell or plant cell having the introduced sequence of the invention is selected using methods known to those of skill in the art such as, but not limited to, Southern blot analysis, DNA sequencing, PCR analysis, or phenotypic analysis. When a plant or plant part is employed in the foregoing embodiments, the plant or plant cell is grown under plant forming conditions for a time sufficient to modulate the concentration and/or activity of the polypeptide conferring glufosinate resistance in the plant. Plant forming conditions are well known in the art and discussed briefly elsewhere herein.

B. Methods of Selecting Host Cells Expressing the Polypeptide that Confers Resistance to Glufosinate In another aspect, the sequence encoding a polypeptide that confers glufosinate resistance (i.e., SEQ ID NO: 1, 2, 3, 4, 5, 6, 7, 8, 9, 10, 11, 12 or active variants or fragments thereof) can also be used as a selectable marker. In this embodiment, the expression of the polypeptide in a cell or organism confers upon the cell or organism the detectable phenotypic trait of glufosinate resistance, thereby allowing one to select for cells or organisms that have been transformed with a gene of interest linked to the sequence that encodes a polypeptide that confers glufosinate resistance.

Thus, for example, a nucleic acid construct comprising the polynucleotide as set forth in SEQ ID NO:2, 4, 6, 8, 10, 12 or an active variant or fragment thereof and further comprising a polynucleotide of interest can be introduced into a host cell. Cells containing the glufosinate resistance sequence can be selected by growing the host cell, transgenic plant or plant cell in the presence of an effective concentration of glufosinate and under conditions where the polypeptide is expressed at an effective level. Transgenic cells expressing the sequence which confers glufosinate resistance and further comprise the polynucleotide of interest grow at a rate that is discernibly greater than the cell would grow if it did not express the selectable marker. In specific embodiments, the concentration of glufosinate in the culture media during selection comprises about 20 mM, 30 mM, 40 mM, 50 mM, 60 mM, 70 mM, 80 mM, 90 mM, 100 mM, 120 mM, 130 mM, 140 mM, 150 mM or greater.

Such methods find use in a variety of host cells including plants, most bacteria (including *E. coli*), actinomycetes, yeasts, algae and fungi. One benefit of using herbicide resistance as a marker in plants, as opposed to conventional antibiotic resistance, is that it obviates the concern of some members of the public that antibiotic resistance might escape into the environment.

C. Method of Producing Crops and Controlling Weeds

Methods for controlling weeds in an area of cultivation, preventing the development or the appearance of herbicide resistant weeds in an area of cultivation, producing a crop, and increasing crop safety are provided. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

Methods provided comprise planting the area of cultivation with a plant or a seed having a heterologous polynucleotide encoding a polypeptide that confer glufosinate resistance or an active variant or fragment thereof, and in specific embodiments, applying to the crop, seed, weed and/or area of cultivation thereof an effective amount of a herbicide of interest. It is recognized that the herbicide can be applied before or after the crop is planted in the area of cultivation. Such herbicide applications can include an application of glufosinate. Generally, the effective amount of herbicide applied to the field is sufficient to selectively control the weeds without significantly affecting the crop.

"Weed" as used herein refers to a plant which is not desirable in a particular area. Conversely, a "crop plant" as used herein refers to a plant which is desired in a particular area, such as, for example, a maize or soybean plant. Thus, in some embodiments, a weed is a non-crop plant or a non-crop species, while in some embodiments, a weed is a crop species which is sought to be eliminated from a particular area, such as, for example, an inferior and/or non-transgenic soybean plant in a field planted with a plant having the heterologous nucleotide sequence encoding the polypeptide that confers glufosinate resistance or an active variant or fragment thereof.

Further provided is a method for producing a crop by growing a crop plant that is resistant to glufosinate or derivative thereof as a result of being transformed with a heterologous polynucleotide encoding SEQ ID NO: 1, 3, 5, 7, 9, 11 or active variant or fragment thereof, under conditions such that the crop plant produces a crop, and harvesting the crop. Preferably, glufosinate is applied to the plant, or in the vicinity of the plant, or in the area of cultivation at a concentration effective to control weeds without preventing the transgenic crop plant from growing and producing the crop. The application of the glufosinate can be before planting, or at any time after planting up to and including the time of harvest. The glufosinate can be applied once or multiple times. The timing of the herbicide application, amount applied, mode of application, and other parameters will vary based upon the specific nature of the crop plant and the growing environment. The invention further provides the crop produced by this method.

Further provided are methods for the propagation of a plant containing a heterologous polynucleotide encoding a polypeptide that confers glufosinate resistance or active variant or fragment thereof. The plant can be, for example, a monocot or a dicot. In one aspect, propagation entails crossing a plant containing the heterologous polynucleotide encoding a polypeptide that confers glufosinate resistance with a second plant, such that at least some progeny of the cross display glufosinate tolerance.

By "treated with a combination of" or "applying a combination of" herbicides to a crop, area of cultivation or field it is intended that a particular field, crop or weed is treated with each of the herbicides and/or chemicals indicated to be part of the combination so that a desired effect is achieved, i.e., so that weeds are selectively controlled while the crop is not significantly damaged. The application of each herbicide and/or chemical may be simultaneous or the applications may be at different times (sequential), so long as the desired effect is achieved. Furthermore, the application can occur prior to the planting of the crop. Classifications of herbicides (i.e., the grouping of herbicides into classes and subclasses) are well-known in the art and include classifications by HRAC (Herbicide Resistance Action Committee) and WSSA (the Weed Science Society of America) (see also, Retzinger and Mallory-Smith (1997) *Weed Technology* 11: 384-393).

Methods of controlling weeds can employ an herbicide or herbicide combination and may further comprise the use of insecticides and/or fungicides, and/or other agricultural chemicals such as fertilizers. The use of such combined treatments of the invention can broaden the spectrum of activity against additional weed species and suppress the proliferation of any resistant biotypes.

VI. Sequence Comparisons

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Additional mathematical algorithms are known in the art and can be utilized for the comparison of two sequences. See, for example, the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLAST programs of Altschul et al. (1990) J. Mol. Biol. 215:403, BLAST nucleotide searches can be performed with the BLASTN program. BLAST protein searches can be performed with the BLASTP program. To obtain gapped alignments for comparison purposes, Gapped BLAST (in BLAST 2.0) can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

As used herein, the term "identity" or "percent identity" when used with respect to a particular pair of aligned amino acid or nucleotide sequences, refers to the percent amino acid sequence identity that is obtained by counting the number of identical matches in the alignment and dividing such number of identical matches by the length of the aligned sequences. As used herein, the term "similarity" or "percent similarity" when used with respect to a particular pair of aligned amino acid sequences or nucleotides sequences, refers to the sum of the scores that are obtained from a scoring matrix for each amino acid pair in the alignment divided by the length of the aligned sequences.

Unless otherwise stated, identity and similarity will be calculated by the Needleman-Wunsch global alignment and scoring algorithms (Needleman and Wunsch, 1970, J. Mol. Biol. 48(3):443-453) as implemented by the "needle" program, distributed as part of the EMBOSS software package (Rice, P. Longden, I. and Bleasby, A., EMBOSS: The European Molecular Biology Open Software Suite, 2000, Trends in Genetics 16, (6) pp 276-277, versions 6.3.1 available from EMBnet at EMBOSS web sites, among other sources) using default gap penalties and scoring matrices (EBLOSUM62 for protein and EDNAFULL for DNA). Equivalent programs may also be used. By "equivalent program" is intended any sequence comparison program that, for any two sequences in question, generates an alignment having identical nucleotide residue matches and an identical percent sequence identity when compared to the corresponding alignment generated by needle from EMBOSS version 6.3.1.

Non-limiting embodiments include:

1. An isolated polynucleotide or a recombinant DNA comprising a nucleotide sequence encoding a polypeptide having
   (a) at least 97% identity to the amino acid sequence set forth in SEQ ID NO: 7, wherein said polypeptide confers glufosinate resistance to a host cell;
   (b) at least 99% identity to the amino acid sequence set forth in SEQ ID NO: 9, wherein said polypeptide confers glufosinate resistance to a host cell; or
   (c) at least 90% identity to the amino acid sequence set forth in SEQ ID NO: 11, wherein said polypeptide confers glufosinate resistance to a host cell.

2. The isolated polynucleotide or recombinant DNA of embodiment 1, wherein said nucleotide sequence encodes the amino acid sequence set forth in SEQ ID NO:7, 9 or 11.

3. A recombinant polynucleotide construct comprising a nucleotide sequence encoding a polypeptide having at least 95% identity to the amino acid sequence set forth in SEQ ID NO: 11, wherein said polypeptide confers glufosinate resistance to a host cell.

4. The recombinant polynucleotide construct of embodiment 3, wherein said nucleotide sequence is operably linked to a promoter.

5. The recombinant polynucleotide construct of embodiment 3 or 4, wherein said recombinant polynucleotide construct further comprise a plasmid.

6. A plant cell comprising a heterologous polynucleotide comprising:
   a) an isolated polynucleotide or a recombinant DNA comprising a nucleotide sequence encoding a polypeptide having at least 90% identity to the amino acid sequence set forth in SEQ ID NO: 1, 3, 7, 9 or 11, wherein said polypeptide confers glufosinate resistance to the cell; or,
   b) a recombinant polynucleotide construct comprising a nucleotide sequence encoding a polypeptide having at least 90% identity to the amino acid sequence set forth in SEQ ID NO: 1, 3, 7, 9 or 11, wherein said polypeptide confers glufosinate resistance to the cell.

7. The plant cell of embodiment 6, wherein said nucleotide sequence encodes the amino acid sequence set forth in SEQ ID NO:1, 3, 7, 9 or 11.

8. The plant cell of embodiment 6, wherein said nucleotide sequence encodes an amino acid sequence having at least 95% sequence identity to SEQ ID NO: 1, 3, 7, 9 or 11.

9. The plant cell of any one of embodiments 6-8, wherein the plant cell exhibits enhanced resistance to glufosinate as compared to a wild type plant cell of the same species, strain or cultivar.

10. The plant cell any one of embodiments 6-9, wherein said plant cell is from a monocot.

11. The plant cell of embodiment 10, wherein said monocot is maize, wheat, rice, barley, sugarcane, sorghum, or rye.

12. The plant cell of any one of embodiments 6-9, wherein said plant cell is from a dicot.

13. The plant cell of embodiment 12, wherein the dicot is soybean, Brassica, sunflower, cotton, or alfalfa.

14. A plant comprising a plant cell of any one of embodiments 6-13.

15. A plant explant comprising a plant cell of any one of embodiments 6-13.

16. A transgenic seed produced by the plant of embodiment 14.

17. A method of producing a plant cell having a heterologous polynucleotide encoding a polypeptide which confers glufosinate resistance to the plant cell comprising transforming said cell with
a) an isolated polynucleotide or a recombinant DNA comprising a nucleotide sequence encoding a polypeptide having at least 90% identity to the amino acid sequence set forth in SEQ ID NO: 1, 3, 7, 9 or 11, wherein said polypeptide confers glufosinate resistance to the cell; or,
b) a recombinant polynucleotide construct comprising a nucleotide sequence encoding a polypeptide having at least 90% identity to the amino acid sequence set forth in SEQ ID NO: 1, 3, 7, 9 or 11, wherein said polypeptide confers glufosinate resistance to the cell.

18. The method of embodiment 17, further comprising selecting a cell which is resistant to glufosinate by growing the transgenic plant or plant cell in the presence of a concentration of glufosinate under conditions where the polypeptide is expressed at an effective level, whereby the transgenic cell grows at a rate that is discernibly greater than the cell would grow if it did not contain the nucleic acid construct.

19. The method of any one of embodiments 17-18, wherein said polynucleotide construct further comprises a polynucleotide sequence of interest.

20. The method of embodiment 18, where said cell is a plant cell.

21. The method of embodiment 20, wherein said plant cell is from a monocot.

22. The method of embodiment 21, wherein said monocot is maize, wheat, rice, barley, sugarcane, sorghum, or rye.

23. The method of embodiment 20, wherein said plant cell is from a dicot.

24. The method of embodiment 23, wherein the dicot is soybean, Brassica, sunflower, cotton, or alfalfa.

25. A method for controlling weeds in a field containing a crop comprising:
(a) applying to an area of cultivation, a crop or a weed in an area of cultivation a sufficient amount of glufosinate to control weeds without significantly affecting the crop; and,
(b) planting the field with the transgenic seeds of embodiment 16 or the plant of embodiment 14.

26. The method of embodiment 25, wherein the glufosinate is applied to the area of cultivation or to said plant.

27. The method of embodiment 25, wherein step (a) occurs before or simultaneously with, or after step (b).

28. The method of any one of embodiments 25-27, wherein said plant is a monocot.

29. The method of embodiment 28, wherein said monocot is maize, wheat, rice, barley, sugarcane, sorghum, or rye.

30. The method of any one of embodiments 25-27, wherein said plant is a dicot.

31. The method of embodiment 30, wherein the dicot is soybean, Brassica, sunflower, cotton, or alfalfa.

EXPERIMENTAL

Introduction

Modern day agriculture relies heavily on development of new crop germplasm and traits that provide protection to crops against various biotic factors; primarily Lepidopteran and Coleopteran pests. Since the introduction of the first transgenic corn to the farming industry, the use of transgenic crops (GMO crops) is continuously rising. First methods for making transgenic plants were reported in 1983, since then various plant species were successfully transformed. A number of plant transformation methods were invented for various plant systems, and the utility of these methods is usually restricted by the particular plant species, resulting in a range of transformation efficiencies (% of healthy transgenic plants recovered at the end of transformation/recovery protocol).

There are two principle DNA delivery mechanisms by which a particular DNA is inserted into the genome of plant cells. The first method is a variation of direct DNA delivery, either by bombardment of the plant tissue with metal particles covered with DNA of interest or using the vacuum to drive the dried DNA fragment into plant tissue. The second and most widely used method utilizes soil bacteria, like Agrobacterium Tumefactions, to deliver part of its plasmid DNA into the plant cell. The usual problems of plant transformation lay in the area of Agrobacterium/plant incapability, "not clean" insertion of DNA, or choice of selectable gene/chemical combination for a particular plant species for selection of transgenic plant.

Example 1

Predicted ORFs (open reading frames) and protein products from genome sequences of several bacterial isolates were identified. A predicted protein was found with 43.53% identity to the phosphinothricin acetyltransferase (PAT) gene. This gene coding for a new GluR (glufosinate resistance) protein was cloned from that strain and is referred to herein as GluRAP1 and set forth in SEQ ID NO:1 (protein sequence) and 2 (DNA sequence). The strain harboring SEQ ID NO: 2 coding for SEQ ID NO: 1 was inoculated on M63 minimal media supplemented with 33 mM glufosinate at 28° C. overnight and exhibited growth. The gene coding for SEQ ID NO: 1 was cloned into the pMAL vector and transformed into TOP10 E. coli cells for protein expression with an N-terminal Maltose Binding Protein. The resulting E. coli clone encoding SEQ ID NO:1 was able to grow in the liquid media with concentrations of glufosinate reaching 100 mM, while control E. coli was not able to tolerate more than 1 mM glufosinate in minimum inhibitory concentration experiments (see FIG. 1). The gene coding for GluRAP1 (SEQ ID NO: 1) was used as a glufosinate resistant selectable marker gene in soybean transformation; it was cloned under the constitutive CAW 35S promoter in vectors designed for Agrobacterium-mediated transformation.

Two methods were used to find genes coding for glufosinate resistance: bioinformatics approach and empirical experimental approach. Several isolated bacterial strains were found by the bioinformatics approach to harbor genes coding for proteins with <50% homology to PAT. These strains were grown on M63 minimal media supplemented with 33 mM glufosinate at 28° C. overnight. A strain of Pseudomonas lutea found in Soybean Roots was able to grow in the presence of glufosinate. The strain exhibited stronger and continuous growth on a plate. Genomic DNA from the strain was analyzed using bioinformatics tools and an ORF (open reading frame) coding for a protein with 43.53% homology to PAT (Phosphinothricin Acetyltransferase from *Streptomyces viridochromogenes*) was found (Block et al. (1978) *The EMBO Journal* 6: 2513-18; Strauch et al. (1988) *Gene* 63: 65-74; Thompson et al. (1987) *The EMBO Journal* 6: 2519-23; Wehrmann et al. (1996) *Nature Biotechnology* 14: 1274-78; White et al. (1990) *Nucleic Acids Research* 18: 1062; and, Wohlleben et al. (1988) *Gene* 70: 25-37).

The strain was subsequently grown with success on 100 mM glufosinate-supplemented M63 minimal media; while the gene coding for a new GluR (glufosinate resistance) protein was cloned from that strain and referred to herein as GluRAP and set forth in SEQ ID NO:1 and 2. The gene coding for SEQ ID NO: 1 was cloned into the pMAL vector ((New England Biolabs product that refers the following Guan et al. (1987) *Gene* 67:21-30; Maina et al. (1988) *Gene* 74: 365-373; Riggs (1990) In F. M. Ausebel, R. Brent, R. E. Kingston, D. D. Moore, J. G. Seidman, J. A. Smith and K. Struhl (Ed.), *Current Protocols in Molecular Biology* 16.6.1-16.6.10, New York: John Wiley & Sons, Inc.; Kellerman et al. (1982) In W. A. Wood (Ed.), *Methods in Enzymology* 90:459-463. New York: Academic Press, LaVallie et al. (1990) in F. M. Ausebel, R. Brent, R. E. Kingston, D. D. Moore, J. G. Seidman, J. A. Smith and K. Struhl (Ed.), *Current Protocols in Molecular Biology* 16.4.1-16.4.17. New York: John Wiley & Sons, Inc; and, Kapust and Waugh (1999) Protein Science 8, 1668-1674) and transformed into TOP10 *E. coli* cells for protein expression with an N-terminal Maltose Binding Protein. The resulting *E. coli* clone was analyzed for the ability to grow in the presence of glufosinate. The *E. coli* clone encoding SEQ ID NO:1 from the strain was able to grow in the liquid media with concentrations of glufosinate reaching 100 mM, while control *E. coli* was not able to tolerate more than 1 mM glufosinate in minimum inhibitory concentration experiments (see FIG. 1). The gene coding for GluRAP1 (SEQ ID NO: 1) was used as the glufosinate resistant selectable marker gene in soybean transformation; it was cloned under the constitutive CaMV 35S promoter in vectors designed for *Agrobacterium*-mediated transformation.

Example 2

Five additional microbial strains with robust growth in the presence of 100 mM glufosinate were selected. The glufosinate resistance conferring sequences encoded by the strain described in example 1 and these additional five strains are shown below in Table 2 and set forth in SEQ ID NOS: 1-12. Table 1 provides the genera (determined from the 16S rRNA gene sequence) and strain designation of the isolate from which the sequences were derived. For expression as recombinant proteins, some of the genes were altered to provide an ATG start codon to ensure expression in *E. coli*. See Table 1 for details. An alignment of SEQ ID NOS: 1, 3, 5, 7, 9, and 11 is provided in FIG. 2.

TABLE 1

| SEQ ID NO | AgB name | Strain | Changes made for *E. coli* expression |
| --- | --- | --- | --- |
| 2 | APG00318 | *Pseudomonas* sp. strain APG00318 | |

TABLE 1-continued

| SEQ ID NO | AgB name | Strain | Changes made for *E. coli* expression |
| --- | --- | --- | --- |
| 4 | APG00037 | *Rhodococcus* sp. strain APG00037 | GTC start changed to ATG for expression |
| 6 | APG00163 | *Stenotrophomonas* sp. strain APG00163 | TGA stop codon changed to TAA for expression |
| 8 | APG00135 | *Flavobacterium* sp. strain APG00135 | |
| 10 | APG00119 | *Serratia* sp. strain APG00119 | GTG start changed to ATG and TGA stop changed to TAA for expression |
| 12 | APG00240 | *Pseudomonas* sp. strain APG00240 | GTG start changed to ATG and TGA stop changed to TAA for expression |

Figure 3:
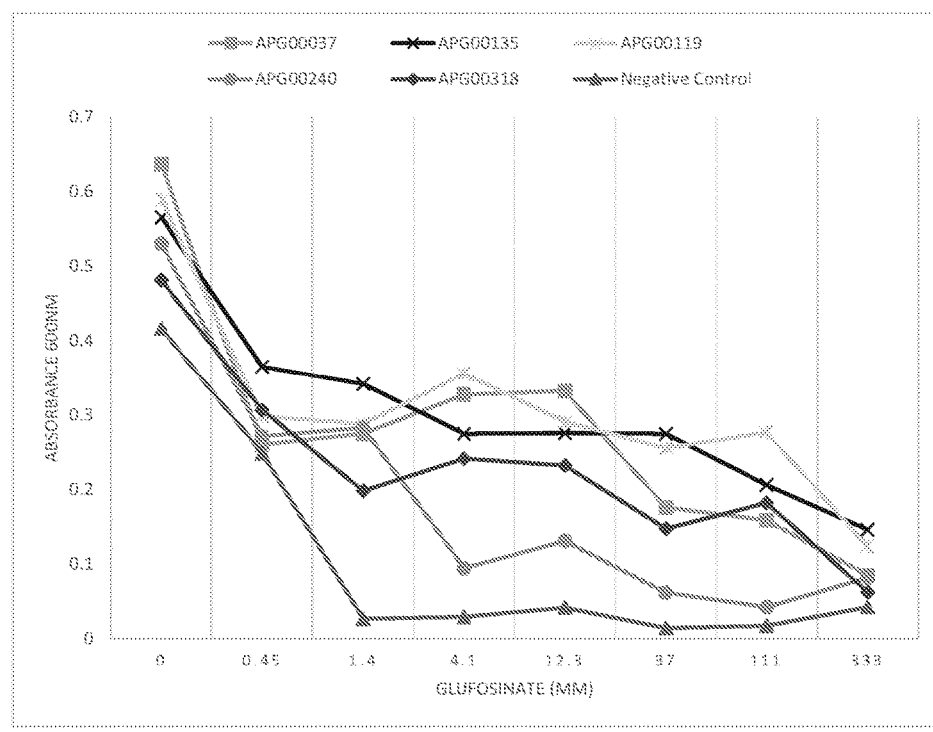
FIG. 3 shows that *E. coli* transformed with sequences coding for the glufosinate-resistant proteins as set forth in SEQ ID NOS: 1, 3, 5, 7, 9, and 11 were able to grow, and shows the ability of the strains to tolerate and continue to grow in the presence of glufosinate.

Genes coding for glufosinate-resistant proteins were cloned as MBP (Maltose Binding Protein) fusions and expressed in *E. coli*. These *E. coli* strains were grown. The ability of the strains to tolerate and continue to grow in the presence of glufosinate was measured under various glufosinate concentrations upon induction of gene expression by addition of IPTG into the media in which the strains were growing. See FIG. 3.

*E. coli* cultures that carry the genes APG00135, APG00119 and APG00318 had higher tolerance level to glufosinate. These three genes were chosen for further studies as selectable markers in plant transformation. They were cloned under control of the 2×35S promoter and used in *Agrobacterium*-mediated soybean transformation (see vector map below).

Figure 4:
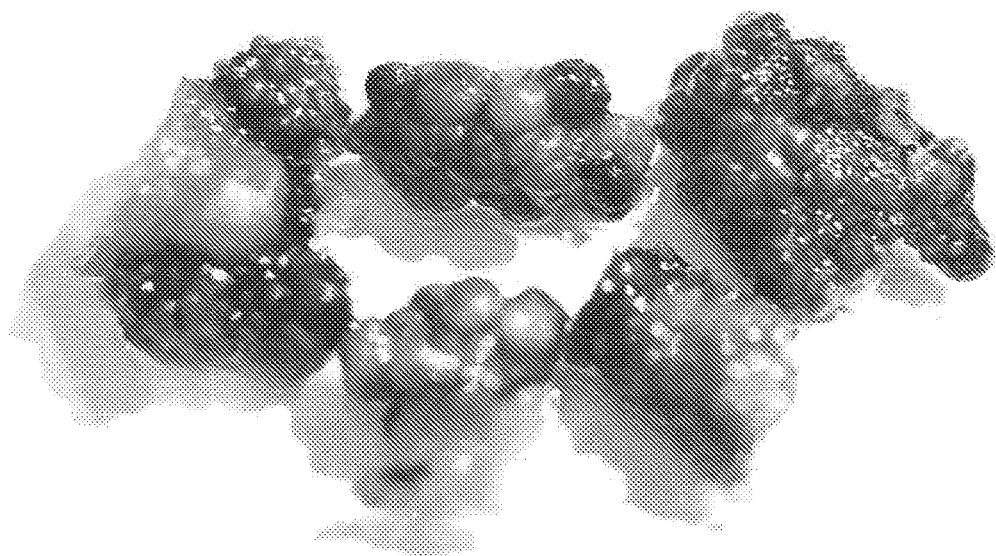
FIG. 4 shows transformed soy callus. Transgenic plants were selected by incubating callus on medium containing 25 uM glufosinate. Glufosinate resistance was observed as soy callus was growing on the media, and the transgenic nature of the callus was confirmed by staining the callus pieces with GUS stain.

Transgenic plants were selected by incubating callus on medium containing 25 uM glufosinate. Glufosinate resistance was observed as soy callus was growing on the media, and the transgenic nature of the callus was confirmed by staining the callus pieces with GUS stain. (FIG. 4) See above for construct pSV37 that carries APG00318 gene.

Example 3

The modes of action for the enzymes conferring glufosinate resistance were investigated to determine if these enzymes acetylate glufosinate, and if they do so at the same site as other known PATs (N-acetylation).

Enzyme assays were run in vitro with enzymes comprising 2 purified candidate PATs (MBP fusions) APG00119 (SEQ ID NO: 9/10) and APG00318 (SEQ ID NO: 1/2) and 2 different substrates: phosphinothricin (glufosinate) and Acetyl-CoA. The time course consisted of "0", 20 min, 1 hr and 3 hr. Results were analyzed by HPLC-MS as follows: (1) acetylation (mass shift); (2) acetylation site (MS-MS fragmentation); and, an unbiased look at most prevalent enzyme-dependent peak. LC/MS detection of N-acetylation of glufosinate by PATs was carried out as follows.

Samples:

Substrates (glufosinate, acetyl CoA) and reaction mixtures were prepared. Reactions were started by adding phosphinothricin (glufosinate) and quenched at the indicated time point by adding 5×HPLC-grade methanol and refrigerating samples.

LC/MS Methods:

Reverse phase LC-EST/MS was performed on a high-resolution TF5600 Quadrupole/Time-Of-Flight mass spectrometer (AB-Sciex) in the negative ion mode.

Procedures:

Samples were diluted 1ox with HPLC-grade methanol 5 uL was injected for LC/MS.

Results:

MS and MS/MS analysis showed that N-acetyl glufosinate was produced by in enzymatic reactions. (Data not shown.)

Example 4. Soybean Transformation

Figure 5:
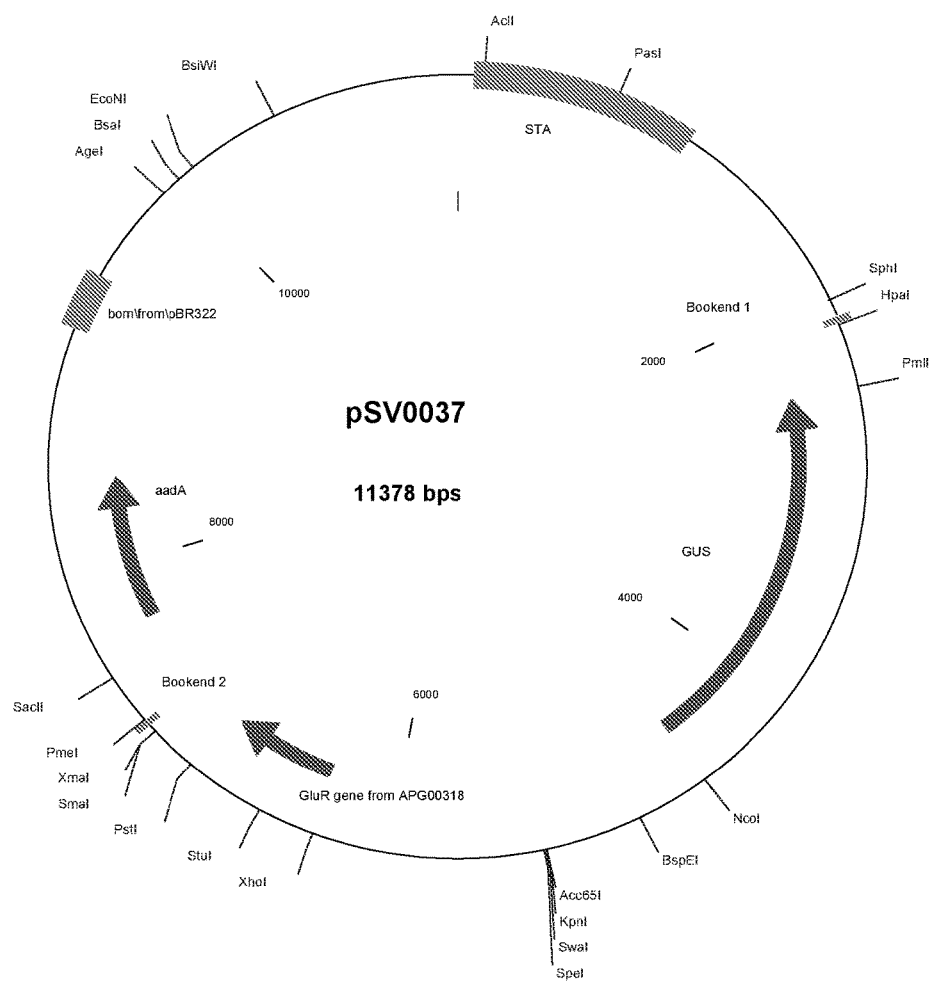
FIG. 5 provides a map of the transformation vector pSV0037.

The various glufosinate resistance sequences encoding by SEQ ID NO: 1, 7, and 9 (APG00318, APG00135, and APG00119 respectively) were cloned into separate plant transformation vectors (pSV0037, pSV0069 and pSV0070) that carried Bookend 1 and Bookend 2 sequences which facilitate the integration of genes of interest into plant genomic DNA. Such transformation vectors, and the Bookend sequences are described in U.S. Provisional App. No. 62/094,782, filed Dec. 19, 2014 and US Utility Application entitled "Sequences to Facilitate Incorporation of DNA into the Genome of an Organism" filed concurrently herewith, both of which are herein incorporated by reference in its entirety. Genetic material between Bookends was composed of two gene cassettes, one cassette with a glufosinate resistant selectable marker (encoding SEQ ID NO: 1, 7, or 9) and one carrying GUS for the easy of transgenesis detection by staining plant material. See, for example, FIG. 5 which shows pSV0037 (expressing SEQ ID NO: 1). Similarly, pSV0069 expressed SEQ ID NO: 7 and psV0070 expressed SEQ ID NO: 9.

Soybean seeds were inoculated and selected as described below.

A. Method of Transformation

Preparation of *Agrobacterium*:

Four days prior to inoculation, several loops of *Agrobacterium* were streaked to a fresh plate of YEP* medium supplemented with the appropriate antibiotics** (spectinomycin, chloramphenicol and kanamycin). Bacteria were grown for two days in the dark at 28 C. After two days, several loops of bacteria were transferred to 3 ml of YEP liquid medium with antibiotics in a 125 ml Erlenmeyer flask. Flasks were placed on a rotary shaker at 250 RPM at 28 C overnight. One day before inoculation, 2-3 ml of the overnight culture were transferred to 125 ml of YEP with antibiotics in a 500 ml Erlenmeyer flask. Flasks were placed on a rotary shaker at 250 RPM at 28 C overnight.

Prior to inoculation, the OD of the bacterial culture was checked at OD 620. An OD of 0.8-1.0 indicated that the culture is in log phase. The culture was centrifuged at 4000 RPM for 10 minutes in Oakridge tubes. The supernatant was discarded and the pellet is re-suspended in a volume of Soybean Infection Medium (SI) to achieve the desired OD. The cultures are held with periodic mixing until needed for inoculation.

Sterilization and Germination of Seeds:

Two or three days prior to inoculation, soybean seeds were surface sterilized using chlorine gas. In a fume hood, a petri dish with seeds was place in a bell jar with the lid off. 1.75 ml of 12 N HCl was slowly added to 100 ml of bleach in a 250 ml Erlenmeyer flask inside the bell jar. The lid was immediately placed on top of the bell jar. Seeds are allowed to sterilize for 14-16 hours (overnight). The top was removed from the bell jar and the lid of the petri dish is replaced. The petri dish with the surface sterilized was then opened in a laminar flow for around 30 minutes to disperse any remaining chlorine gas.

Seeds were imbibed with either sterile DI water or soybean infection medium (SI) for 1-2 days. Twenty to 30 seeds were covered with liquid in a 100×25 mm petri dish and incubated in the dark at 24 C. After imbibition, non-germinating seeds were discarded.

Preparation of Soybean Cotyledonary Explants:

Cotyledonary explants were processed on a sterile paper plate with sterile filter paper dampened using SI medium. Cotyledonary explants were prepared employing techniques in the art. See, for example, U.S. Pat. No. 7,473,822, herein incorporated by reference.

Inoculation of Soybean Cotyledonary Explants:

Typically, 16-20 cotyledons were inoculated per treatment. The SI medium used for holding the explants was discarded and replaced with 25 ml of *Agrobacterium* culture (OD 620=0.8–20). After all explants were submerged, the inoculation was carried out for 30 minutes with periodic swirling of the dish. After 30 minutes, the *Agrobacterium* culture was removed.

Co-Cultivation of Soybean Cotyledonary Explants:

Co-cultivation plates were prepared by overlaying one piece of sterile paper onto Soybean Co-cultivation Medium (SCC). Without blotting, the inoculated cotyledons were cultured adaxial side down on the filter paper. Around 20 explants can be cultured on each plate. The plates were sealed with Parafilm and cultured at 24 C and around 120 umoles m-2 s-1 (in a Percival incubator) for 4-5 days.

Shoot Induction of Soybean Cotyledonary Explants:

After co-cultivation, the cotyledons were washed 3 times in 25 ml of Soybean Wash Medium with 200 mg/l of cefotaxime and timentin. The cotyledons were blotted on sterile filter paper and then transferred to Soybean Shoot Induction Medium (SSI). The nodal end of the explant was depressed slightly into the medium with distal end kept above the surface at about 45 deg. No more than 10 explants were cultured on each plate. The plates were wrapped with Micropore tape and cultured in the Percival at 24 C and around 120 umoles m-2 s-1.

The explants were transferred to fresh SSI medium after 14 days. Emerging shoots from the shoot apex and cotyledonary node were discarded. Shoot induction was continued for another 14 days under the same conditions.

Shoot Elongation of Soybean Cotyledonary Explants:

After 4 weeks of shoot induction, the cotyledon was separated from the nodal end and a parallel cut is made underneath the area of shoot induction (shoot pad). The area of the parallel cut was placed on Soybean Shoot Elongation Medium (SSE) and the explants cultured in the Percival at 24 C and around 120 umoles m-2 s-1. This step was repeated every two weeks for up to 8 weeks as long as shoots continue to elongate.

Rooting of Transgenic Shoots:

When shoots reach a length of 2-3 cm, they were transferred to Soybean Rooting Medium (SR) in a Plantcon vessel and incubated under the same conditions for 2 weeks or until roots reach a length of around 3-4 cm. After this, plants were transferred to soil.

B. Selection of Transgenic Plants

After approximately 12 weeks of selection, leaf pieces from surviving shoots were excised and treated with X-glucuronide. Transgenic shoots comprising each of constructs pSV0037, pSV0069 and pSV0070 stained blue (GUS+) after incubating overnight. Transgenic shoot were obtained after transformation with each of the constructs. (Data not shown).

Note, all media mentioned for soybean transformation are found in Paz et al. (2010) *Agrobacterium*-mediated transformation of soybean and recovery of transgenic soybean plants; Plant Transformation Facility of Iowa State University, which is herein incorporated by reference in its entirety. (See, agron-www.agron.iastate.edu/ptf/protocol/Soybean.pdf)

Example 5. Transformation of Maize

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000.times. Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. In the dark. However, it is not necessary per se to incubate the embryos overnight.

The resulting explants are transferred to mesh squares (30-40 per plate), transferred onto osmotic media for about 30-45 minutes, then transferred to a beaming plate. (See, for example, PCT Publication No, WO/0138514 and U.S. Pat. No. 5,240,842). DNA constructs designed to express a polypeptide conferring glufosinate resistance of the present invention in plant cells are accelerated into plant tissue using an aerosol beam accelerator, using conditions essentially as described in PCI Publication No. WO/0138514. After beaming, embryos are incubated for about 30 min on osmotic media, and placed onto incubation media overnight at 25° C. In the dark. To avoid unduly damaging beamed explants, they are incubated for at least 24 hours prior to transfer to recovery media. Embryos are then spread onto recovery period media, for about 5 days, 25° C. In the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

TABLE 2

Summary of SEQ ID NOS.

| SEQ ID NO | Designation | AgB name | Organism | sequence |
|---|---|---|---|---|
| 1 | AA | AGP00318 | Pseudomonas sp. strain APG00318 | MSKTTVRIAQVSDAQAIQAIYAPMVESTTISFELEPPSVE EMAMRIESTLLTYPYLVAVRDGQVIGYAYASQHRAREA YRWSVDVTVYISPEAHRSGVGRALYDVILLPTLKKQGFH AAYAGIALPNDGSVGLHEALGFAHIGTYPEVGFKHGAW RDVGYWRIALDSTNPPKLPVLFSEISLF |
| 2 | NT | AGP00318 | Pseudomonas sp. strain APG00318 | ATGAGCAAGACGACAGTAAGGATTGCGCAGGTTTCGG ACGCTCAAGCCATCCAGGCAATCTACGCACCAATGGT TGAGAGCACTACGATTTCGTTCGAGCTTGAGCCGCCTT CAGTCGAAGAGATGGCCATGCGGATTGAGTCGACTCT GCTAACTTACCCGTACCTGGTTGCGGTGCGAGACGGC CAGGTCATCGGCTATGCATATGCCAGTCAGCACCGGG CTCGTGAGGCCTATCGCTGGTCGGTCGACGTCACCGTT TATATATCGCCAGAAGCGCACCGTAGTGGCGTCGGTC GGGCACTGTATGACGTGTTGCTGCCAACATTGAAGAA GCAAGGTTTTCACGCAGCCTATGCCGGGATCGCTCTG CCCAATGATGGCAGCGTGGGACTACACGAAGCACTTG GCTTCGCTCACATTGGTACGTATCCAGAAGTAGGATT CAAGCATGGCGCTTGGCGTGATGTTGGATATTGGCGT ATCGCGCTGGATTCAACGAATCCGCCAAAACTGCCCG TGCTTTTCAGTGAGATCAGTCTCTTCTGA |
| 3 | AA | APG00037 | Rhodococcus sp. strain APG00037 | MLIRDTVTEDLPSILDIHNDAIRNTTAIWDETEVGLDERM DWLDGRLRAGYPVLTAVVDGAVAGYASYAQWRPKSG YRLTVEHSVYVGSDFHRRGIASALMAELIARASAAGIHA LVGVIESRNTTSIALHEKFGFVTVGQMPEVGIKFDRWLD LTLMQLTL |
| 4 | NT | APG00037 | Rhodococcus sp. strain APG00037 | atgctgatcagagacaccgtcaccgaagatctcccgtcgattctcgacatccacaacgac gccatccggaacacgacggcaatctgggacgaaaccgaagtcggtctcgacgagcgg atggactggctcgacggccgactccgcgccggataccccgtgctcaccgcagtcgtcg acggcgcagtcgcgggtacgcgtcgtacgcgcagtggcgcccgaagagcggatacc gtctcaccgtcgaacattccgtgtacgtcggtagcgacttccaccgtcgcggaatcgcca gcgccttgatggccgaactgatcgcccgggcatccgccgcggggatccatgcgctcgtc ggggtcatcgaatcacgaaacacgacgtcgatagcgctgcacgagaagttcggattcgt caccgtcgggcagatgcccgaggtcggcatcaagttcgaccggtggctcgatctcacctt gatgcagttgacgctctaa |
| 5 | AA | APG00163 | Stenotrophomonas sp. strain APG00163 | MAVLIRDAGPADIAAITAIYAVEVTDFVNTYEYDIPDASE MLRRMRDIIDRGFPYLVAEIDGQVAGYAYANTYRTRVA YQWTVENSVYVDAAFQGKGVGTGLLQALIDACVARGY RQMVAVIGEPTNTASIKLHERFGFELVGVFRGLGRKHGR WLDTVQMQRALGDGADTAPSNE |

TABLE 2-continued

Summary of SEQ ID NOS.

| SEQ ID NO | Desig- nation | AgB name | Organism | sequence |
|---|---|---|---|---|
| 6 | NT | AP G00163 | *Stenotrophomonas* sp. strain APG 00163 | atggccgtcctcatccgtgatgccggcccggccgacatcgccgcgatcaccgcgatcta cccggtggaagtgaccgacttcgtcaacacctacgagtacgacatcccggacgcgtccg agatgctgcgccgcatgcgcgacatcatcgatcgcggcttcccctacctggtcgccgag attgacgccaggtggccggctatgcctacgccaacacctaccgcacccgcgttgccta ccagtggacccggaaaactcggtctacgtcgatgccgcctccagggcaagggcgttg gcaccggcctgctccaggccctcatcgacgcctgcgtggcgcgtggctaccggcagat ggtcgcggtgatcgccgaaccgaccaataccgcttcaatcaagctgcacgaacccttcg gcttcgagctggtcggcgtgttccgtggcctcggccgcaagcatggccgaggctggat actttgcagatgcagcgcgcgctcggcgatggcgccgacaccgcaccttccaatgaat |
| 7 | AA | APG00135 | *Flavobacterium* sp. strain APG00135 | MSVILRPATVNDLEKILEIVNHSILHTTANYSYDIQTIEVQ TKWFEDKKAKNLPIVVADLDGEVVGFGSYGQFREKIGY QYTVEHSVYVVDNVIGKGIGSKLLTELIRLAKEQGYHV MIGAIDADNAGSITFHEKFGFVATGTIREVGYKFDHWLD LVFMQLILK |
| 8 | NT | APG00135 | *Flavobacterium* sp. strain APG00135 | atgagcgttatacttagacctgcgactgtaaatgatttagaaaaaatccttgaaattgttaa tcattctattctgcatacaacagcaaattacagttatgatattcaaactattgaggtgcaaa cgaaatggtttgaagataaaaaagccaaaaaccttcctattgtagtagccgatttagacgg cgaagttgttggttttggaagctacggccaatttagagaaaaaattggttatcaatatactgt agagcattctgtttatgttgttgataatgtgattggaaaaggcataggatcaaaattattaa ccgaattaatccgtctggcaaaagagcagggttatcacgttatgattggtgctatcgacgct gataatgcaggaagcattacttttcatgaaaagtttggttttgtggcaacaggaaccattcg tgaagttggctataaattcgatcattggcttgatcttgttttatgcagctaatcttgaaat aa |
| 9 | AA | APG00119 | *Serratia* sp. strain APG00119 | MTTLSAPVLSLLDATPDDMAAVLRIYTQHVLYGAASFE EQPPTLAEMQLRLSKVREAGLPWLVAKSAGVIVGYCYA TPYRPRPAYRFTVEDSVYIAEGQQGKGIGRALLSALIARC EQGPWRQMLAIVGDSAANRGSLAHQSLGFTSAGTLKA VGFKLGEWRDTQIMQRALGAGGNRHP |
| 10 | NT | APG00119 | *Serratia* sp. strain APG00119 | atgacaacgctctccgccccgtactcagccttcttgacgccacaccggacgatatggcc gccgtgctgcgtatttacacccagcacgtgctgtacggcgcgggcctcgtttgaagagcag ccgccgacgctggcggaaatgcagctgcgcctgagcaaggtgcgggaggccggcctg ccctggctggtggcgaaaagcgcaggcgtcattgtgggttactgttatgccacgccttatc gccccgaccggcttaccgcgcttaccgtggaagactcggtgtacatcgccgaagggcaa cagggtaaaggcatcggcagagcgcttctgagcgccttgatcgcccgctgcgaacaag gccctggcgccagatgctggcgatcgtcggcgattccgccgccaaccgcggctcattg gccttgcatcagtcactcggcttcaccagtgcagggacgttaaaagcggtggggttcaag ctgggggaatggcgcgacgcagattatgcagcgcgcgctgggcgcggggcggcaat cggcatccttaa |
| 11 | AA | APG00240 | *Pseudomonas* sp. strain APG00240 | MKTNMTYTIRDALLTDMPAVLDIYNDAVLNTTAIWNEQ PVDLGNREAWFAARQTQAYPILVVVDDAGQVLGYSSFG DWRPFEGFRHTVEHSVYVRADQRGNGLGPLLMTALIER ARTCDKHMMVAAIESGNAASIHLHQKQGFITTGQMPQV GTKFGRWLDLTFMQLDLSPGASAPPSQAPASTPVA |
| 12 | NT | APG00240 | *Pseudomonas* sp. strain APG00240 | atgaaaacgaacatgacgtatacgattcgtgacgcgctgctgactgacatgcctgccgtg ctggacatctacaacgacgccgtcctcaacaccacggcgatctggaacgaacaaccggt ggacctgggcaatcgtgaagcctggttcgctgcgcgccagacccaggcctatccgattct ggtggtcgttgacgacgcaggtcaggtgctgggctactcctcgttcggcgactggcgcc ccttcgaaggctttcgtcacacggtcgagcattctgtctatgtgcgcgccgaccagcgtgg caacggcttgggtccgctgctgatgactgcgctgatcgaacgcgcgcagaacctgcgaca aacacatgatggttgccgccatcgaaagcggtaatgcggcgtcgattcacctgcaccaaa agcagggtttcattactaccggccagatgccgcaagtcggcaccaagttcggtcgctggc tggacctgactttcatgcaactggacctgtctccgggcgcatccgcaccgccgtcacagg cgccggcatcaacacccgtggcttaa |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide or a recombinant DNA comprising a nucleotide sequence encoding a polypeptide having
    (a) at least 97% identity to the amino acid sequence set forth in SEQ ID NO: 7, wherein said polypeptide confers glufosinate resistance to a host cell;
    (b) at least 99% identity to the amino acid sequence set forth in SEQ ID NO: 9, wherein said polypeptide confers glufosinate resistance to a host cell; or
    (c) at least 90% identity to the amino acid sequence set forth in SEQ ID NO: 11, wherein said polypeptide confers glufosinate resistance to a host cell;
    wherein said recombinant DNA comprises a heterologous promoter operably linked to the nucleotide sequence.

2. The isolated polynucleotide or recombinant DNA of claim 1, wherein said nucleotide sequence encodes the amino acid sequence set forth in SEQ ID NO:7, 9 or 11.

3. The isolated polynucleotide or recombinant DNA construct of claim 1, comprising a nucleotide sequence encoding a polypeptide having at least 95% identity to the amino acid sequence set forth in SEQ ID NO: 11, wherein said polypeptide confers glufosinate resistance to a host cell.

4. The isolated polynucleotide or recombinant DNA construct of claim 1, comprising a nucleotide sequence encoding a polypeptide having at least 98% identity to the amino acid sequence set forth in SEQ ID NO: 11, wherein said polypeptide confers glufosinate resistance to a host cell.

5. The isolated polynucleotide or recombinant DNA construct of claim 1, wherein said recombinant polynucleotide construct further comprises a plasmid.

6. A plant cell comprising a heterologous polynucleotide comprising
    a recombinant polynucleotide construct comprising a nucleotide sequence encoding a polypeptide having at least 90% identity to the amino acid sequence set forth in SEQ ID NO: 3, 7 or 11 or at least 96% identity to the amino acid sequence set forth in SEQ ID NO:9, wherein said polypeptide confers glufosinate resistance to the cell.

7. The plant cell of claim 6, wherein said nucleotide sequence encodes the amino acid sequence set forth in SEQ ID NO: 3, 7, 9 or 11.

8. The plant cell of claim 6, wherein said nucleotide sequence encodes an amino acid sequence having at least 95% sequence identity to SEQ ID NO: 3, 7, or 11 or at least 96% identity to the amino acid sequence set forth in SEQ ID NO:9.

9. The plant cell of claim 6, wherein the plant cell exhibits enhanced resistance to glufosinate as compared to a wild type plant cell of the same species, strain or cultivar.

10. The plant cell of claim 6, wherein said plant cell is from a monocot.

11. The plant cell of claim 6, wherein said plant cell is from a dicot.

12. A plant comprising a plant cell of claim 6.

13. A plant explant comprising a plant cell of claim 6.

14. A transgenic seed comprising the heterologous polynucleotide produced by the plant of claim 12.

15. A method of producing a plant cell having a heterologous polynucleotide encoding a polypeptide which confers glufosinate resistance to the plant cell comprising transforming said plant cell with
    a) an isolated polynucleotide or a recombinant DNA comprising a nucleotide sequence encoding a polypeptide having at least 90% identity to the amino acid sequence set forth in SEQ ID NO: 3, 7, or 11 or at least 96% identity to the amino acid sequence set forth in SEQ ID NO:9, wherein said polypeptide confers glufosinate resistance to the cell; or,
    b) a recombinant polynucleotide construct comprising a nucleotide sequence encoding a polypeptide having at least 90% identity to the amino acid sequence set forth in SEQ ID NO: 3, 7, or 11 or at least 96% identity to the amino acid sequence set forth in SEQ ID NO:9, wherein said polypeptide confers glufosinate resistance to the cell.

16. The method of claim 15, further comprising selecting a cell which is resistant to glufosinate by growing the transgenic plant or plant cell in the presence of a concentration of glufosinate under conditions where the polypeptide is expressed at an effective level, whereby the transgenic cell grows at a rate that is discernibly greater than the cell would grow if it did not contain the nucleic acid construct.

17. The method of claim 15, wherein said polynucleotide construct further comprises a polynucleotide sequence of interest.

18. The method of claim 16, where said cell is a plant cell.

19. The method of claim 18, wherein said plant cell is from a monocot.

20. The method of claim 18, wherein said plant cell is from a dicot.

21. A method for controlling weeds in a field containing a crop comprising:

(a) applying to an area of cultivation, a crop or a weed in an area of cultivation a sufficient amount of glufosinate to control weeds without significantly affecting the crop; and, (b) planting the field with the plant of claim 12 or a transgenic seed produced from said plant.

22. A host cell comprising a recombinant DNA comprising a nucleotide sequence encoding a polypeptide having (a) at least 97% identity to the amino acid sequence set forth in SEQ ID NO: 7, wherein said polypeptide confers glufosinate resistance to a host cell;

(b) at least 99% identity to the amino acid sequence set forth in SEQ ID NO: 9, wherein said polypeptide confers glufosinate resistance to a host cell; or (c) at least 90% identity to the amino acid sequence set forth in SEQ ID NO: 11, wherein said polypeptide confers glufosinate resistance to a host cell;

wherein said recombinant DNA comprises a heterologous promoter operably linked to the nucleotide sequence.

* * * * *

SEQUENCE LISTING

```
<160> NUMBER OF SEQ ID NOS: 12

<210> SEQ ID NO 1
<211> LENGTH: 182
<212> TYPE: PRT
<213> ORGANISM: Pseudomonas sp. strain APG00318

<400> SEQUENCE: 1

Met Ser Lys Thr Thr Val Arg Ile Ala Gln Val Ser Asp Ala Gln Ala
1               5                   10                  15

Ile Gln Ala Ile Tyr Ala Pro Met Val Glu Ser Thr Thr Ile Ser Phe
            20                  25                  30

Glu Leu Glu Pro Pro Ser Val Glu Glu Met Ala Met Arg Ile Glu Ser
        35                  40                  45

Thr Leu Leu Thr Tyr Pro Tyr Leu Val Ala Val Arg Asp Gly Gln Val
    50                  55                  60

Ile Gly Tyr Ala Tyr Ala Ser Gln His Arg Ala Arg Glu Ala Tyr Arg
65                  70                  75                  80

Trp Ser Val Asp Val Thr Val Tyr Ile Ser Pro Glu Ala His Arg Ser
                85                  90                  95

Gly Val Gly Arg Ala Leu Tyr Asp Val Leu Leu Pro Thr Leu Lys Lys
            100                 105                 110

Gln Gly Phe His Ala Ala Tyr Ala Gly Ile Ala Leu Pro Asn Asp Gly
        115                 120                 125

Ser Val Gly Leu His Glu Ala Leu Gly Phe Ala His Ile Gly Thr Tyr
    130                 135                 140

Pro Glu Val Gly Phe Lys His Gly Ala Trp Arg Asp Val Gly Tyr Trp
145                 150                 155                 160

Arg Ile Ala Leu Asp Ser Thr Asn Pro Pro Lys Leu Pro Val Leu Phe
                165                 170                 175

Ser Glu Ile Ser Leu Phe
            180

<210> SEQ ID NO 2
<211> LENGTH: 549
<212> TYPE: DNA
<213> ORGANISM: Pseudomonas sp. strain APG00318

<400> SEQUENCE: 2
atgagcaaga cgacagtaag gattgcgcag gtttcggacg ctcaagccat ccaggcaatc     60
tacgcaccaa tggttgagag cactacgatt tcgttcgagc ttgagccgcc ttcagtcgaa    120
gagatggcca tgcggattga gtcgactctg ctaacttacc cgtacctggt tgcggtgcga    180
gacggccagg tcatcggcta tgcatatgcc agtcagcacc gggctcgtga ggcctatcgc    240
tggtcggtcg acgtcaccgt ttatatatcg ccagaagcgc accgtagtgg cgtcggtcgg    300
gcactgtatg acgtgttgct gccaacattg aagaagcaag ttttcacgc agcctatgcc     360 gggatcgctc tgcccaatga tggcagcgtg ggactacacg aagcacttgg cttcgctcac    420
```

```
attggtacgt atccagaagt aggattcaag catggcgctt ggcgtgatgt tggatattgg    480
cgtatcgcgc tggattcaac gaatccgcca aaactgcccg tgcttttcag tgagatcagt    540
ctcttctga                                                            549
```

<210> SEQ ID NO 3
<211> LENGTH: 162
<212> TYPE: PRT
<213> ORGANISM: Rhodococcus sp. strain APG00037

<400> SEQUENCE: 3

```
Met Leu Ile Arg Asp Thr Val Thr Glu Asp Leu Pro Ser Ile Leu Asp
1               5                   10                  15

Ile His Asn Asp Ala Ile Arg Asn Thr Thr Ala Ile Trp Asp Glu Thr
            20                  25                  30

Glu Val Gly Leu Asp Glu Arg Met Asp Trp Leu Asp Gly Arg Leu Arg
        35                  40                  45

Ala Gly Tyr Pro Val Leu Thr Ala Val Val Asp Gly Ala Val Ala Gly
    50                  55                  60

Tyr Ala Ser Tyr Ala Gln Trp Arg Pro Lys Ser Gly Tyr Arg Leu Thr
65                  70                  75                  80

Val Glu His Ser Val Tyr Val Gly Ser Asp Phe His Arg Arg Gly Ile
                85                  90                  95

Ala Ser Ala Leu Met Ala Glu Leu Ile Ala Arg Ala Ser Ala Ala Gly
            100                 105                 110

Ile His Ala Leu Val Gly Val Ile Glu Ser Arg Asn Thr Thr Ser Ile
        115                 120                 125

Ala Leu His Glu Lys Phe Gly Phe Val Thr Val Gly Gln Met Pro Glu
    130                 135                 140

Val Gly Ile Lys Phe Asp Arg Trp Leu Asp Leu Thr Leu Met Gln Leu
145                 150                 155                 160

Thr Leu
```

<210> SEQ ID NO 4
<211> LENGTH: 489
<212> TYPE: DNA
<213> ORGANISM: Rhodococcus sp. strain APG00037

<400> SEQUENCE: 4

```
atgctgatca gagacaccgt caccgaagat ctcccgtcga ttctcgacat ccacaacgac    60
gccatccgga acacgacggc aatctgggac gaaaccgaag tcggtctcga cgagcggatg    120
gactggctcg acggccgact ccgcgccgga taccccgtgc tcaccgcagt cgtcgacggc    180
gcagtcgcgg ggtacgcgtc gtacgcgcag tggcgcccga agagcggata ccgtctcacc    240
gtcgaacatt ccgtgtacgt cggtagcgac ttccaccgtc gcggaatcgc cagcgccttg    300
atggccgaac tgatcgcccg gcatccgcc gcggggatcc atgcgctcgt cggggtcatc    360
gaatcacgaa acacgacgtc gatagcgctg cacgagaagt tcggattcgt caccgtcggg    420
cagatgcccg aggtcggcat caagttcgac cggtggctcg atctcacctt gatgcagttg    480
acgctctaa                                                            489
```

<210> SEQ ID NO 5
<211> LENGTH: 176
<212> TYPE: PRT
<213> ORGANISM: Stenotrophomonas sp. strain APG00163

<400> SEQUENCE: 5

Met Ala Val Leu Ile Arg Asp Ala Gly Pro Ala Asp Ile Ala Ile
1               5                  10                 15

Thr Ala Ile Tyr Ala Val Glu Val Thr Asp Phe Val Asn Thr Tyr Glu
            20                  25                  30

Tyr Asp Ile Pro Asp Ala Ser Glu Met Leu Arg Arg Met Arg Asp Ile
            35                  40                  45

Ile Asp Arg Gly Phe Pro Tyr Leu Val Ala Glu Ile Asp Gly Gln Val
    50                  55                  60

Ala Gly Tyr Ala Tyr Ala Asn Thr Tyr Arg Thr Arg Val Ala Tyr Gln
65              70                  75                  80

Trp Thr Val Glu Asn Ser Val Tyr Val Asp Ala Ala Phe Gln Gly Lys
                85                  90                  95

Gly Val Gly Thr Gly Leu Leu Gln Ala Leu Ile Asp Ala Cys Val Ala
            100                 105                 110

Arg Gly Tyr Arg Gln Met Val Ala Val Ile Gly Glu Pro Thr Asn Thr
        115                 120                 125

Ala Ser Ile Lys Leu His Glu Arg Phe Gly Phe Glu Leu Val Gly Val
    130                 135                 140

Phe Arg Gly Leu Gly Arg Lys His Gly Arg Trp Leu Asp Thr Val Gln
145                 150                 155                 160

Met Gln Arg Ala Leu Gly Asp Gly Ala Asp Thr Ala Pro Ser Asn Glu
                165                 170                 175

<210> SEQ ID NO 6
<211> LENGTH: 531
<212> TYPE: DNA
<213> ORGANISM: Stenotrophomonas sp. strain APG00163

<400> SEQUENCE: 6
atggccgtcc tcatccgtga tgccggcccg ccgacatcg ccgcgatcac cgcgatctac      60
gcggtggaag tgaccgactt cgtcaacacc tacgagtacg acatcccgga cgcgtccgag     120
atgctgcgcc gcatgcgcga catcatcgat cgcggcttcc cctacctggt cgccgagatt     180
gacggccagg tggccggcta tgcctacgcc aacacctacc gcacccgcgt tgcctaccag     240
tggaccgtgg aaaactcggt ctacgtcgat gccgcgttcc agggcaaggg cgttggcacc     300
ggcctgctcc aggccctcat cgacgcctgc gtggcgcgtg ctaccggca gatggtggcg      360 gtgatcggcg aaccgaccaa taccgcttca atcaagctgc acgaacgctt cggcttcgag     420
ctggtcggcg tgttccgtgg cctcggccgc aagcatggcc gctggctgga taccgtgcag     480
atgcagcgcg cgctcggcga tggcgccgac accgcacctt ccaatgaata a              531

<210> SEQ ID NO 7
<211> LENGTH: 165
<212> TYPE: PRT
<213> ORGANISM: Flavobacterium sp. strain APG00135

<400> SEQUENCE: 7

Met Ser Val Ile Leu Arg Pro Ala Thr Val Asn Asp Leu Glu Lys Ile
1               5                   10                  15

Leu Glu Ile Val Asn His Ser Ile Leu His Thr Thr Ala Asn Tyr Ser
            20                  25                  30

Tyr Asp Ile Gln Thr Ile Glu Val Gln Thr Lys Trp Phe Glu Asp Lys
        35                  40                  45

Lys Ala Lys Asn Leu Pro Ile Val Val Ala Asp Leu Asp Gly Glu Val
    50                  55                  60

Val Gly Phe Gly Ser Tyr Gln Phe Arg Glu Lys Ile Gly Tyr Gln
65                  70                  75                  80

Tyr Thr Val Glu His Ser Val Tyr Val Asp Asn Val Ile Gly Lys
                85                  90                  95

Gly Ile Gly Ser Lys Leu Leu Thr Glu Leu Ile Arg Leu Ala Lys Glu
            100                 105                 110

Gln Gly Tyr His Val Met Ile Gly Ala Ile Asp Ala Asp Asn Ala Gly
            115                 120                 125

Ser Ile Thr Phe His Glu Lys Phe Gly Phe Val Ala Thr Gly Thr Ile
    130                 135                 140

Arg Glu Val Gly Tyr Lys Phe Asp His Trp Leu Asp Leu Val Phe Met
145                 150                 155                 160

Gln Leu Ile Leu Lys
                165

<210> SEQ ID NO 8
<211> LENGTH: 498
<212> TYPE: DNA
<213> ORGANISM: Flavobacterium sp. strain APG00135

<400> SEQUENCE: 8
atgagcgtta tacttagacc tgcgactgta aatgatttag aaaaaatcct tgaaattgtt     60
aatcattcta ttctgcatac aacagcaaat tacagttatg atattcaaac tattgaggtg    120
caaacgaaat ggtttgaaga taaaaaagcc aaaaaccttc ctattgtagt agccgattta    180
gacggcgaag ttgttggttt tggaagctac ggccaattta gagaaaaaat tggttatcaa    240
tatactgtag agcattctgt ttatgttgtt gataatgtga ttggaaaagg cataggatca    300
aaattattaa ccgaattaat ccgtctggca aaagagcagg gttatcacgt tatgattggt    360
gctatcgacg ctgataatgc aggaagcatt acttttcatg aaaagtttgg ttttgtggca    420
acaggaacca ttcgtgaagt tggctataaa ttcgatcatt ggcttgatct tgtttttatg    480
cagctaatct tgaaataa                                                  498

<210> SEQ ID NO 9
<211> LENGTH: 180
<212> TYPE: PRT
<213> ORGANISM: Serratia sp. strain APG00119

<400> SEQUENCE: 9

Met Thr Thr Leu Ser Ala Pro Val Leu Ser Leu Leu Asp Ala Thr Pro
1               5                   10                  15

Asp Asp Met Ala Ala Val Leu Arg Ile Tyr Thr Gln His Val Leu Tyr
            20                  25                  30

Gly Ala Ala Ser Phe Glu Glu Gln Pro Pro Thr Leu Ala Glu Met Gln
        35                  40                  45

Leu Arg Leu Ser Lys Val Arg Glu Ala Gly Leu Pro Trp Leu Val Ala
    50                  55                  60

Lys Ser Ala Gly Val Ile Val Gly Tyr Cys Tyr Ala Thr Pro Tyr Arg
65                  70                  75                  80

Pro Arg Pro Ala Tyr Arg Phe Thr Val Glu Asp Ser Val Tyr Ile Ala
                85                  90                  95

Glu Gly Gln Gln Gly Lys Gly Ile Gly Arg Ala Leu Leu Ser Ala Leu
            100                 105                 110

Ile Ala Arg Cys Glu Gln Gly Pro Trp Arg Gln Met Leu Ala Ile Val
        115                 120                 125

Gly Asp Ser Ala Ala Asn Arg Gly Ser Leu Ala Leu His Gln Ser Leu
        130                 135                 140

Gly Phe Thr Ser Ala Gly Thr Leu Lys Ala Val Gly Phe Lys Leu Gly
145                 150                 155                 160

Glu Trp Arg Asp Thr Gln Ile Met Gln Arg Ala Leu Gly Ala Gly Gly
                165                 170                 175

Asn Arg His Pro
            180

<210> SEQ ID NO 10
<211> LENGTH: 543
<212> TYPE: DNA
<213> ORGANISM: Serratia sp. strain APG00119

<400> SEQUENCE: 10
atgacaacgc tctccgcccc cgtactcagc cttcttgacg ccacaccgga cgatatggcc        60
gccgtgctgc gtatttacac ccagcacgtg ctgtacggcg cggcctcgtt tgaagagcag       120
ccgccgacgc tggcggaaat gcagctgcgc ctgagcaagg tgcgggaggc cggcctgccc       180
tggctggtgg cgaaaagcgc aggcgtcatt gtgggttact gttatgccac gccttatcgc       240
ccccgaccgg cttaccgctt taccgtggaa gactcggtgt acatcgccga agggcaacag       300
ggtaaaggca tcggcagagc gcttctgagc gccttgatcg cccgctgcga acaaggcccc       360
tggcgccaga tgctggcgat cgtcggcgat ccgccgccaa ccgcggctc attggccttg        420 catcagtcac tcggcttcac cagtgcaggg acgttaaaag cggtggggtt caagctgggg       480
gaatggcgcg acacgcagat tatgcagcgc gcgctgggcg cgggcggcaa tcggcatcct       540
taa                                                                    543

<210> SEQ ID NO 11
<211> LENGTH: 187
<212> TYPE: PRT
<213> ORGANISM: Pseudomonas sp. strain APG00240

<400> SEQUENCE: 11

Met Lys Thr Asn Met Thr Tyr Thr Ile Arg Asp Ala Leu Leu Thr Asp
1               5                   10                  15

Met Pro Ala Val Leu Asp Ile Tyr Asn Asp Ala Val Leu Asn Thr Thr
            20                  25                  30

Ala Ile Trp Asn Glu Gln Pro Val Asp Leu Gly Asn Arg Glu Ala Trp
        35                  40                  45

Phe Ala Ala Arg Gln Thr Gln Ala Tyr Pro Ile Leu Val Val Val Asp
    50                  55                  60

Asp Ala Gly Gln Val Leu Gly Tyr Ser Ser Phe Gly Asp Trp Arg Pro
65                  70                  75                  80

Phe Glu Gly Phe Arg His Thr Val Glu His Ser Val Tyr Val Arg Ala
                85                  90                  95

Asp Gln Arg Gly Asn Gly Leu Gly Pro Leu Leu Met Thr Ala Leu Ile
            100                 105                 110

Glu Arg Ala Arg Thr Cys Asp Lys His Met Met Val Ala Ala Ile Glu
        115                 120                 125

Ser Gly Asn Ala Ala Ser Ile His Leu His Gln Lys Gln Gly Phe Ile
    130                 135                 140

Thr Thr Gly Gln Met Pro Gln Val Gly Thr Lys Phe Gly Arg Trp Leu
145                 150                 155                 160

-continued

```
Asp Leu Thr Phe Met Gln Leu Asp Leu Ser Pro Gly Ala Ser Ala Pro
                165                 170                 175

Pro Ser Gln Ala Pro Ala Ser Thr Pro Val Ala
            180                 185

<210> SEQ ID NO 12
<211> LENGTH: 564
<212> TYPE: DNA
<213> ORGANISM: Pseudomonas sp. strain APG00240

<400> SEQUENCE: 12
atgaaaacga acatgacgta tacgattcgt gacgcgctgc tgactgacat gcctgccgtg      60
ctggacatct acaacgacgc cgtcctcaac accacggcga tctggaacga acaaccggtg     120
gacctgggca atcgtgaagc ctggttcgct gcgcgccaga cccaggccta tccgattctg     180
gtggtcgttg acgacgcagg tcaggtgctg ggctactcct cgttcggcga ctggcgcccc     240
ttcgaaggct ttcgtcacac ggtcgagcat tctgtctatg tgcgcgccga ccagcgtggc     300
aacggcttgg gtccgctgct gatgactgcg ctgatcgaac gcgccagaac ctgcgacaaa     360
cacatgatgg ttgccgccat cgaaagcggt aatgcggcgt cgattcacct gcaccaaaag     420
cagggtttca ttactaccgg ccagatgccg caagtcggca ccaagttcgg tcgctggctg     480
gacctgactt tcatgcaact ggacctgtct ccgggcgcat ccgcaccgcc gtcacaggcg     540
ccggcatcaa cacccgtggc ttaa                                            564
```